(12) United States Patent
Arensdorf et al.

(10) Patent No.: US 8,802,131 B2
(45) Date of Patent: Aug. 12, 2014

(54) DEVICES AND METHODS FOR DELIVERING ACTIVE AGENTS TO THE OSTEOMEATAL COMPLEX

(75) Inventors: Patrick A. Arensdorf, Palo Alto, CA (US); Danielle L. Biggs, Hoover, AL (US); Rodney Brenneman, San Juan Capistrano, CA (US); David B. Downie, Cupertino, CA (US); Donald J. Eaton, Los Altos, CA (US); Thomas R. Tice, Indian Springs, AL (US)

(73) Assignee: Intersect ENT, Inc., Menlo Park, CA (US)

(*) Notice: Subject to any disclaimer, the term of this patent is extended or adjusted under 35 U.S.C. 154(b) by 1082 days.

(21) Appl. No.: 12/541,840

(22) Filed: Aug. 14, 2009

(65) Prior Publication Data

US 2009/0306624 A1    Dec. 10, 2009

Related U.S. Application Data

(63) Continuation of application No. 11/775,157, filed on Jul. 9, 2007, now Pat. No. 8,535,707.

(60) Provisional application No. 60/819,825, filed on Jul. 10, 2006.

(51) Int. Cl.
*A61F 13/00* (2006.01)

(52) U.S. Cl.
USPC .......................................... 424/434; 424/422

(58) Field of Classification Search
None
See application file for complete search history.

(56) References Cited

U.S. PATENT DOCUMENTS

| | | |
|---|---|---|
| 374,026 A | 11/1887 | Williams |
| 2,096,162 A | 10/1937 | Daley |
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,894,539 A | 7/1975 | Tallent |
| 3,903,893 A | 9/1975 | Scheer |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,650,488 A | 3/1987 | Bays et al. |
| 4,655,771 A | 4/1987 | Wallsten |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,886,493 A | 12/1989 | Yee |
| 4,941,881 A | 7/1990 | Masters et al. |
| 4,964,850 A | 10/1990 | Bouton et al. |
| 5,011,474 A | 4/1991 | Brennan |
| 5,035,706 A | 7/1991 | Giantureo et al. |
| 5,116,311 A | 5/1992 | Löfstedt |
| 5,139,510 A | 8/1992 | Goldsmith, III et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,336,163 A | 8/1994 | DeMane et al. |
| 5,342,296 A | 8/1994 | Persson et al. |
| 5,348,553 A | 9/1994 | Whitney |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,512,055 A | 4/1996 | Domb et al. |
| 5,538,738 A | 7/1996 | Ritter et al. |
| 5,632,762 A | 5/1997 | Myler |

(Continued)

FOREIGN PATENT DOCUMENTS

| | | |
|---|---|---|
| AU | 2008/201495 A1 | 10/2008 |
| DE | 101 05 592 A1 | 8/2002 |

(Continued)

OTHER PUBLICATIONS

Becker, Daniel G., The minimally Invasive, Endoscopic Approach to Sinus Surgery, Journal of Long-Term Effects of Medical Implants, 13(3), (2003), pp. 207-221.*

Eberhart, R. C. et al. (2003). *J. Biomater. Sci. Polymer Edn*, 14(4):299-312.

Final Office Action mailed on Jan. 8, 2009, for U.S. Appl. No. 10/800,162, filed Mar. 12, 2004, 5 pages.

Final Office Action mailed on Jul. 22, 2009, for U.S. Appl. No. 11/398,342, filed Apr. 4, 2006, 8 pages.

(Continued)

*Primary Examiner* — Scott Long
*Assistant Examiner* — Lyndsey Beckhardt
(74) *Attorney, Agent, or Firm* — Morrison & Foerster LLP

(57) ABSTRACT

Described here are devices, methods, and kits for treating sinusitis and related respiratory conditions by locally delivering active agents to the osteomeatal complex over a sustained period of time. The devices may be passively fixed within the osteomeatal complex and/or include one or more features that actively fix it within the osteomeatal complex. The devices may optionally include a portion that extends into a sinus ostium, sinus cavity, and/or the nasal passage to deliver an active agent.

13 Claims, 23 Drawing Sheets

(56) References Cited

U.S. PATENT DOCUMENTS

| | | |
|---|---|---|
| 5,645,584 A | 7/1997 | Suyama |
| 5,664,567 A | 9/1997 | Linder |
| 5,672,179 A | 9/1997 | Garth et al. |
| 5,693,065 A | 12/1997 | Rains, III |
| 5,713,855 A | 2/1998 | Shippert |
| 5,746,224 A | 5/1998 | Edwards |
| 5,792,100 A | 8/1998 | Shantha |
| 5,800,379 A | 9/1998 | Edwards |
| 5,800,429 A | 9/1998 | Edwards |
| 5,899,878 A | 5/1999 | Glassman |
| 5,928,190 A | 7/1999 | Davis |
| 6,033,436 A | 3/2000 | Steinke et al. |
| 6,054,122 A | 4/2000 | MacPhee et al. |
| 6,092,528 A | 7/2000 | Edwards |
| 6,113,641 A | 9/2000 | Leroy et al. |
| 6,123,697 A | 9/2000 | Shippert |
| 6,149,944 A | 11/2000 | Jeong et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,224,626 B1 | 5/2001 | Steinke |
| 6,228,111 B1 | 5/2001 | Törmälä et al. |
| 6,280,413 B1 | 8/2001 | Clark et al. |
| 6,297,227 B1 | 10/2001 | Johnson |
| 6,302,875 B1 | 10/2001 | Makower et al. |
| 6,306,084 B1 | 10/2001 | Pinczower |
| 6,342,068 B1 | 1/2002 | Thompson |
| 6,350,465 B1 | 2/2002 | Jonnalagadda et al. |
| 6,355,032 B1 | 3/2002 | Hovda et al. |
| 6,375,615 B1 | 4/2002 | Flaherty et al. |
| 6,447,539 B1 | 9/2002 | Nelson et al. |
| 6,491,940 B1 | 12/2002 | Levin |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,565,597 B1 | 5/2003 | Fearnot et al. |
| 6,606,995 B1 | 8/2003 | Sadek et al. |
| 6,618,921 B1 | 9/2003 | Thornton |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,074,426 B2 | 7/2006 | Kochinke |
| 7,108,706 B2 | 9/2006 | Hogle |
| RE39,321 E | 10/2006 | MacPhee et al. |
| 7,195,016 B2 | 3/2007 | Loyd et al. |
| 7,235,099 B1 | 6/2007 | Duncavage et al. |
| 7,249,390 B2 | 7/2007 | Yale et al. |
| RE39,923 E | 11/2007 | Blom |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,641,644 B2 | 1/2010 | Chang et al. |
| 7,641,688 B2 | 1/2010 | Lesh |
| 7,645,272 B2 | 1/2010 | Chang et al. |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 2002/0051793 A1 | 5/2002 | Drabick |
| 2002/0051845 A1* | 5/2002 | Mehta et al. .................. 427/2.1 |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0133877 A1 | 7/2003 | Levin |
| 2003/0135970 A1 | 7/2003 | Thornton |
| 2003/0147954 A1 | 8/2003 | Yang et al. |
| 2003/0195459 A1 | 10/2003 | Shippert |
| 2003/0203030 A1 | 10/2003 | Ashton et al. |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2005/0038497 A1 | 2/2005 | Neuendorf et al. |
| 2005/0043706 A1 | 2/2005 | Eaton et al. |
| 2005/0131525 A1 | 6/2005 | Hartley |
| 2005/0143817 A1 | 6/2005 | Hunter et al. |
| 2005/0203605 A1 | 9/2005 | Dolan |
| 2005/0229670 A1 | 10/2005 | Perreault |
| 2005/0240147 A1* | 10/2005 | Makower et al. .......... 604/96.01 |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0142736 A1 | 6/2006 | Hissink et al. |
| 2006/0162722 A1 | 7/2006 | Boehm et al. |
| 2006/0210605 A1 | 9/2006 | Chang et al. |
| 2006/0265042 A1 | 11/2006 | Catanese, III et al. |
| 2006/0276871 A1 | 12/2006 | Lamson et al. |
| 2007/0005094 A1 | 1/2007 | Eaton et al. |
| 2007/0100435 A1 | 5/2007 | Case et al. |
| 2007/0129751 A1 | 6/2007 | Muni et al. |
| 2007/0135789 A1 | 6/2007 | Chang et al. |
| 2007/0156211 A1 | 7/2007 | Ferren et al. |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |

(56) References Cited

U.S. PATENT DOCUMENTS

| | | |
|---|---|---|
| 2007/0293946 A1 | 12/2007 | Gonzales et al. |
| 2007/0297186 A1 | 12/2007 | Hoover et al. |
| 2008/0015540 A1 | 1/2008 | Muni et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0047326 A1 | 2/2009 | Eaton et al. |
| 2009/0047327 A1 | 2/2009 | Eaton et al. |
| 2009/0056709 A1 | 3/2009 | Worsoff |
| 2009/0093823 A1 | 4/2009 | Chang et al. |
| 2009/0156980 A1 | 6/2009 | Eaton et al. |
| 2009/0177272 A1 | 7/2009 | Abbate et al. |
| 2009/0187098 A1 | 7/2009 | Makower et al. |
| 2009/0192488 A1 | 7/2009 | Eaton et al. |
| 2009/0192489 A1 | 7/2009 | Eaton et al. |
| 2009/0192490 A1 | 7/2009 | Eaton et al. |
| 2009/0192491 A1 | 7/2009 | Eaton et al. |
| 2009/0192492 A1 | 7/2009 | Eaton et al. |
| 2009/0198179 A1 | 8/2009 | Abbate et al. |
| 2009/0198216 A1 | 8/2009 | Muni et al. |
| 2009/0220571 A1 | 9/2009 | Eaton et al. |
| 2009/0227945 A1 | 9/2009 | Eaton et al. |
| 2009/0238859 A1 | 9/2009 | Eaton et al. |
| 2009/0240112 A1 | 9/2009 | Goldfarb et al. |
| 2009/0312745 A1 | 12/2009 | Goldfarb et al. |
| 2010/0043197 A1 | 2/2010 | Abbate et al. |
| 2011/0004192 A1 | 1/2011 | Eaton et al. |
| 2011/0004193 A1 | 1/2011 | Eaton et al. |
| 2011/0004194 A1 | 1/2011 | Eaton et al. |
| 2011/0004195 A1 | 1/2011 | Eaton et al. |
| 2011/0004196 A1 | 1/2011 | Eaton et al. |
| 2011/0021986 A1 | 1/2011 | Zamboni |
| 2011/0167964 A1 | 7/2011 | Price |
| 2012/0101429 A1 | 4/2012 | Eaton et al. |

FOREIGN PATENT DOCUMENTS

| | | |
|---|---|---|
| EP | 0 761 251 A1 | 3/1997 |
| EP | 1 415 671 A1 | 5/2004 |
| JP | 2-500521 A | 2/1990 |
| JP | 6-506672 A | 7/1994 |
| JP | 8-117326 A | 5/1996 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-97/36949 A1 | 10/1997 |
| WO | WO-99/20261 A2 | 4/1999 |
| WO | WO-99/20261 A3 | 4/1999 |
| WO | WO-01/02024 A2 | 1/2001 |
| WO | WO-01/02024 C1 | 1/2001 |
| WO | WO-01/26658 A2 | 4/2001 |
| WO | WO-01/26658 A3 | 4/2001 |
| WO | WO-03/099359 A1 | 12/2003 |
| WO | WO 2004/082525 * | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/067451 A2 | 6/2007 |
| WO | WO-2007/067451 A3 | 6/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/033533 A2 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A2 | 6/2009 |
| WO | WO-2009/079418 A3 | 6/2009 |
| WO | WO-2010/014834 A1 | 2/2010 |

OTHER PUBLICATIONS

Final Office Action mailed on Jul. 8, 2010, for U.S. Appl. No. 11/398,342, filed Apr. 4, 2006, 7 pages.
Final Office Action mailed on Aug. 18, 2010, for U.S. Appl. No. 11/775,157, filed Jul. 9, 2007, twelve pages.
Final Office Action mailed on Jan. 27, 2011, for U.S. Appl. No. 12/479,794, filed Jun. 6, 2009, 6 pages.
Final Office Action mailed on Nov. 28, 2011, for U.S. Appl. No. 12/883,071, filed Sep. 15, 2010, seven pages.
Final Office Action mailed on Mar. 1, 2012, for U.S. Appl. No. 12/270,695, filed Nov. 13, 2008, 26 pages.
Final Office Action mailed on Apr. 12, 2012, for U.S. Appl. No. 12/883,087, filed Sep. 15, 2010, seven pages.
Final Office Action mailed on Apr. 16, 2012, for U.S. Appl. No. 12/334,373, filed Dec. 12, 2008, seven pages.
Final Office Action mailed on May 29, 2012, for U.S. Appl. No. 12/334,382, filed Dec. 12, 2008, seven pages.
Hietala, E-M. et al. (2001). "Biodegradation of the Copolymeric Polylactide Stent," *Journal of Vascular Research* 38:361-369.

(56) References Cited

OTHER PUBLICATIONS

Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.

International Search Report mailed on Mar. 19, 2008, for PCT Patent Application No. PCT/US2007/015813, filed on Jul. 10, 2007, three pages.

Laaksovirta, S. (Aug. 22, 2003). Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results, Academic Dissertation, Medical School of the University of Tampere, 79 pages.

Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii*, two pages.

Lavigne, F. et al. (May 2002). "Intrasinus Administration of Topical Budesonide to Allergic Patients With Chronic Rhinosinusitis Following Surgery," *The Laryngoscope* 112, seven pages.

Min, Y-G. et al. (1995). "Application of Polylactic Acid Polymer in the Treatment of Acute Maxillary Sinusitis in Rabbits," *Acta Otolaryngol.* 115:548-552.

Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.

Murphy, J.G. et al. (1992). "Precutaneous Polymeric Stents in Porcine Coronary Arteries: Initial Experience With Polyethylene Tereplthalate Stents," *Circulation* 86:1596-1604.

Nguyen, K.T. et al. (2004). "Biomaterials and Stent Technology," Chapter 5 in *Tissue Engineering and Novel Delivery Systems*, 24 pages.

Non-Final Office Action mailed on Jun. 6, 2008, for U.S. Appl. No. 10/800,162, filed Mar. 12, 2004, 5 pages.

Non-Final Office Action mailed on Nov. 25, 2008, for U.S. Appl. No. 11/398,342, filed Apr. 4, 2006, 10 pages.

Non-Final Office Action mailed on Sep. 22, 2009, for U.S. Appl. No. 12/419,927, filed Apr. 7, 2009, 4 pages.

Non-Final Office Action mailed on Sep. 22, 2009, for U.S. Appl. No. 12/419,943, filed Apr. 7, 2009, 5 pages.

Non-Final Office Action mailed on Sep. 22, 2009, for U.S. Appl. No. 12/419,930, filed Apr. 7, 2007, 4 pages.

Non-Final Office Action mailed on Sep. 22, 2009, for U.S. Appl. No. 12/419,937, filed Apr. 7, 2009, 4 pages.

Non-Final Office Action mailed on Sep. 22, 2009, for U.S. Appl. No. 12/419,925, filed Apr. 7, 2009, 4 pages.

Non-Final Office Action mailed on Nov. 13, 2009, for U.S. Appl. No. 11/398,342, filed Apr. 4, 2006, 9 pages.

Non-Final Office Action mailed on Dec. 9, 2009, for U.S. Appl. No. 11/775,157, filed Jul. 9, 2007, twelve pages.

Non-Final Office Action mailed on Jul. 1, 2010, for U.S. Appl. No. 12/479,794, filed Jun. 6, 2009, 5 pages.

Non-Final Office Action mailed on Sep. 10, 2010, for U.S. Appl. No. 12/437,374, filed May 7, 2009, eight pages.

Non-Final Office Action mailed on Nov. 12, 2010, for U.S. Appl. No. 11/398,342, filed Apr. 4, 2006, 8 pages.

Non-Final Office Action mailed on Nov. 23, 2010, for U.S. Appl. No. 12/258,277, filed Oct. 24, 2008, 9 pages.

Non-Final Office Action mailed on Nov. 23, 2010, for U.S. Appl. No. 12/258,282, filed Oct. 24, 2008, 7 pages.

Non-Final Office Action mailed on Nov. 24, 2010, for U.S. Appl. No. 12/883,090, filed Sep. 15, 2010, 7 pages.

Non-Final Office Action mailed on Nov. 24, 2010, for U.S. Appl. No. 12/883,056, filed Sep. 15, 2010, 7 pages.

Non-Final Office Action mailed on Nov. 24, 2010, for U.S. Appl. No. 12/883,079, filed Sep. 15, 2010, 8 pages.

Non-Final Office Action mailed on Mar. 22, 2011, for U.S. Appl. No. 12/883,071, filed Sep. 15, 2010, eight pages.

Non-Final Office Action mailed on May 13, 2011, for U.S. Appl. No. 12/883,087, filed Sep. 15, 2010, seven pages.

Non-Final Office Action mailed on Jun. 14, 2011, for U.S. Appl. No. 12/437,374, filed May 7, 2009, eight pages.

Non-Final Office Action mailed on Jun. 21, 2011, for U.S. Appl. No. 12/270,695, filed Nov. 13, 2008, 24 pages.

Non-Final Office Action mailed on Jul. 13, 2011, for U.S. Appl. No. 12/334,373, filed Dec. 12, 2008, eight pages.

Non-Final Office Action mailed on Sep. 26, 2011, for U.S. Appl. No. 12/334,382, filed Dec. 12, 2008, seven pages.

Non-Final Office Action mailed on May 11, 2012, for U.S. Appl. No. 12/883,071, filed Sep. 15, 2010, seven pages.

Non-Final Office Action mailed on Jun. 7, 2012, for U.S. Appl. No. 12/334,395, filed Dec. 12, 2008, seven pages.

Notice of Allowance mailed on Dec. 23, 2009, for U.S. Appl. No. 12/419,925, filed Apr. 7, 2009, 2 pages.

Notice of Allowance mailed on Dec. 23, 2009, for U.S. Appl. No. 12/419,943, filed Apr. 7, 2009, 2 pages.

Notice of Allowance mailed on Dec. 24, 2009, for U.S. Appl. No. 12/419,927, filed Apr. 7, 2009, 2 pages.

Notice of Allowance mailed on Jan. 19, 2010, for U.S. Appl. No. 12/419,930, filed Apr. 7, 2009, 2 pages.

Notice of Allowance mailed on Feb. 2, 2010, for U.S. Appl. No. 12/419,937, filed Apr. 7, 2009, 2 pages.

Notice of Allowance mailed on Mar. 18, 2011, for U.S. Appl. No. 12/258,277, filed Oct. 24, 2008, seven pages.

Notice of Allowance mailed on Mar. 21, 2011, for U.S. Appl. No. 12/258,282, filed Oct. 24, 2008, eight pages.

Notice of Allowance mailed on Mar. 21, 2011, for U.S. Appl. No. 12/883,059, filed Sep. 15, 2010, ten pages.

Notice of Allowance mailed on Mar. 23, 2011, for U.S. Appl. No. 12/883,079, filed Sep. 15, 2010, nine pages.

Notice of Allowance mailed on Mar. 25, 2011 for U.S. Appl. No. 12/883,090, filed Sep. 15, 2010, eight pages.

Notice of Allowance mailed on Mar. 25, 2011, for U.S. Appl. No. 12/883,056, filed Sep. 15, 2010, eight pages.

Notice of Allowance mailed on Jul. 13, 2011, for U.S. Appl. No. 11/398,342, filed Apr. 4, 2006, seven pages.

Notice of Allowance mailed on Nov. 9, 2011, for U.S. Appl. No. 12/479,794, filed Jun. 6, 2009, seven pages.

Notice of Allowance mailed on Aug. 20, 2012, for U.S. Appl. No. 12/437,374, filed May 7, 2009, eight pages.

Notice of Allowance mailed on Nov. 2, 2012, for U.S. Appl. No. 11/775,157, filed Jul. 9, 2007, eight pages.

Nuutinen, J-P. et al. (2002). "Mechanical Properties and in vitro Degradation of Bioresorbable Knitted Stents," *J. Biomater. Sci. Polymer Edn.* 13(12):1313-1323.

Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.

Parviainen, M. et al. (2000). "A New Biodegradable Stent for the Pancreaticojejunal Anastomosis After Pancreaticoduodenal Resection: In Vitro Examination and Pilot Experiences in Humans," *Pancreas* 21(1):14-21.

Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.

Piskunov, S. et al. (1993). "The Prolongation of Drug Action in the Treatment of Diseases of the Nose and Paranasal Sinuses," *Rhinology* 31:33-36.

Roumestan, C. et al. (2003). "Fluticasone Propionate and Mometasone Furoate Have Equivalent Transcriptional Potencies," *Clinical and Experimental Allergy* 33: 895-901.

Shikani, A.H. (Aug. 1996). "Use of Antibiotics for Expansion of the Merocel® Packing Following Endoscopic Sinus Surgery," *ENT Journal* 75(8):524-528.

Su, S-H. et al. (2003). "Expandable Bioresorbable Endovascular Stent. I. Fabrication and Properties," *Annals of Biomedical Engineering* 31:667-677.

(56) References Cited

OTHER PUBLICATIONS

Tamai, H. et al. (1999). "A Biodegradable Ploy-/-lactic Acid Coronary Stent in the Porcine Coronary Artery," *Journal of Interventional Cardiology* 12(6):443-450.

Thierry, B. et al. (Nov./Dec. 2003, e-pub. Oct. 7, 2003). "Bioactive Coatings of Endovascular Stents Based on Polyelectrolyte Multilayers," *Biomacromolecules* 4:1564-1571.

Toffel, P.H. (Mar. 2001). "The Balanced Philosophy of Secure Mutltimodal Endoscopic Sinus Surgery and Adjunct Sue of Middle Meatal Stenting and Middle Turbinate Modification, Operative Techniques in Otolaryngology," *Head and Neck Surgery* 12(1):40-45.

Vogt. F. et al. (2004). "Long-Term Assessment of a Novel Biodegradable Paclitaxel-Eluting Coronary Polylactide Stent," *European Heart Journal* 25:330-1340.

Final Office Action mailed on Sep. 10, 2013, for U.S. Appl. No. 12/334,395, filed Dec. 12, 2008, 8 pages.

Non-Final Office Action mailed on Mar. 15, 2013, for U.S. Appl. No. 12/512,855, filed Jul. 30, 2009, 10 pages.

Non-Final Office Action mailed on Sep. 23, 2013, for U.S. Appl. No. 12/883,087, filed Sep. 15, 2010, 7 pages.

Notice of Allowance mailed on May 22, 2013, for U.S. Appl. No. 11/775,157, filed Jul. 9, 2007, 10 pages.

Notice of Allowance mailed on Jul. 15, 2013, for U.S. Appl. No. 12,334,382, filed Dec. 12, 2008, 9 pages.

Notice of Allowance mailed on Jul. 30, 2013, for U.S. Appl. No. 12/334,373, filed Dec. 12, 2008, 10 pages.

Notice of Allowance mailed on Sep. 19, 2013, for U.S. Appl. No. 12/883,071, filed Sep. 15, 2010, 6 pages.

* cited by examiner

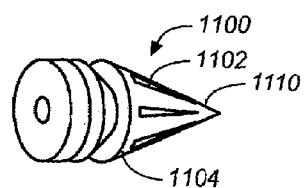
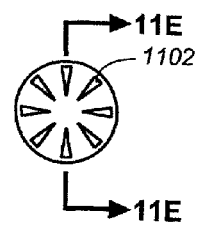
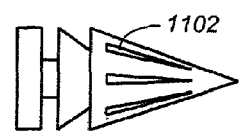
FIG. 11A  FIG. 11B  FIG. 11D
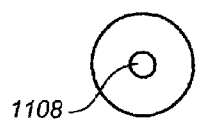
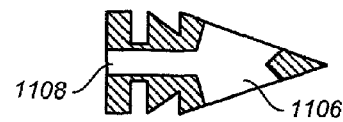
FIG. 11C  FIG. 11E
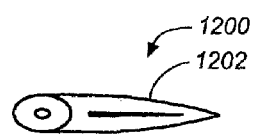
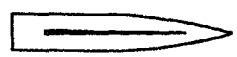
FIG. 12A  FIG. 12B  FIG. 12D
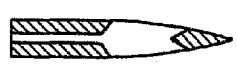
FIG. 12C  FIG. 12E
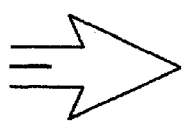
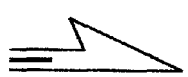
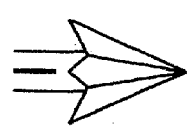
FIG. 12F  FIG. 12G  FIG. 12H

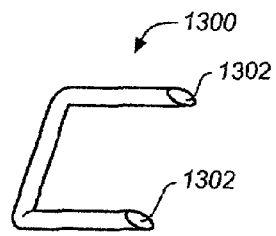
FIG. 13A     FIG. 13B     FIG. 13C
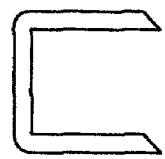
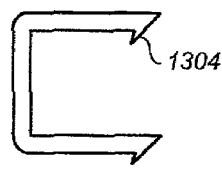
FIG. 13D     FIG. 13E
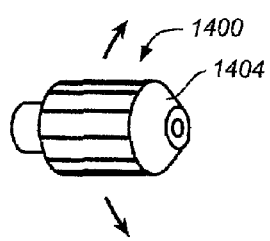
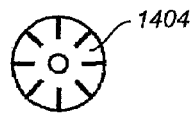
FIG. 14A     FIG. 14B     FIG. 14C
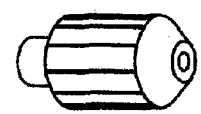
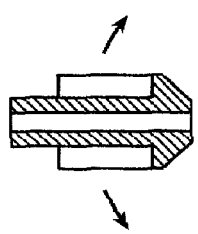
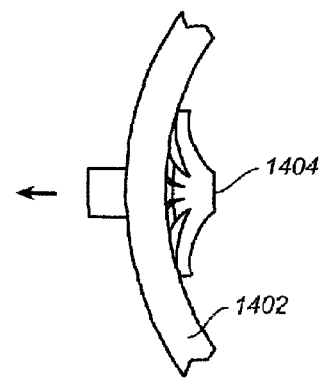
FIG. 14D     FIG. 14E     FIG. 14F

FIG. 19
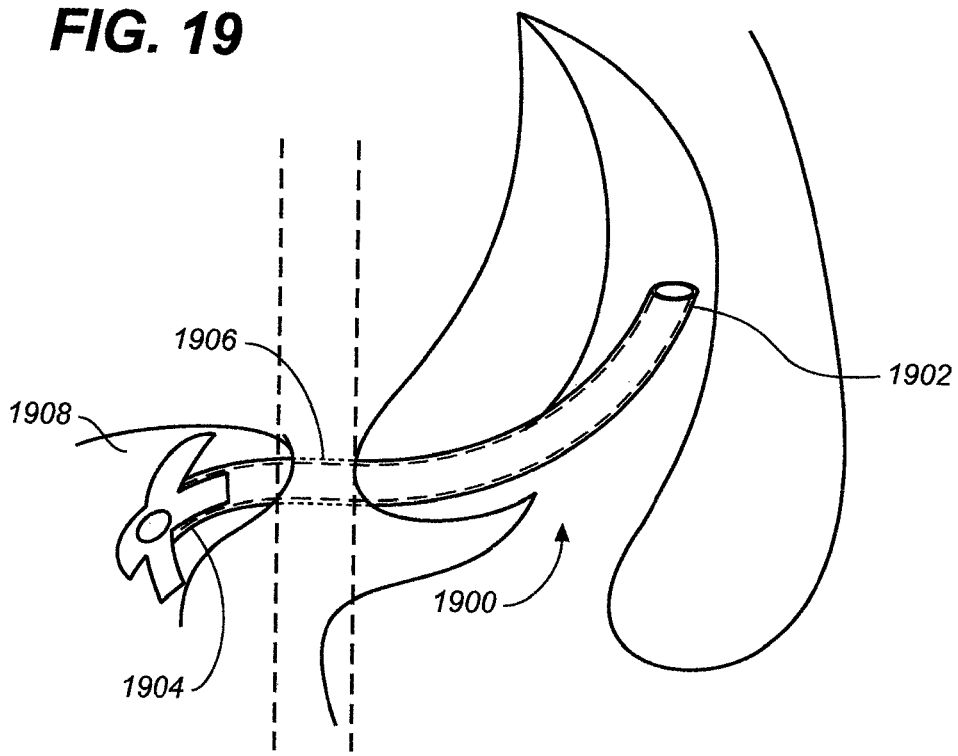
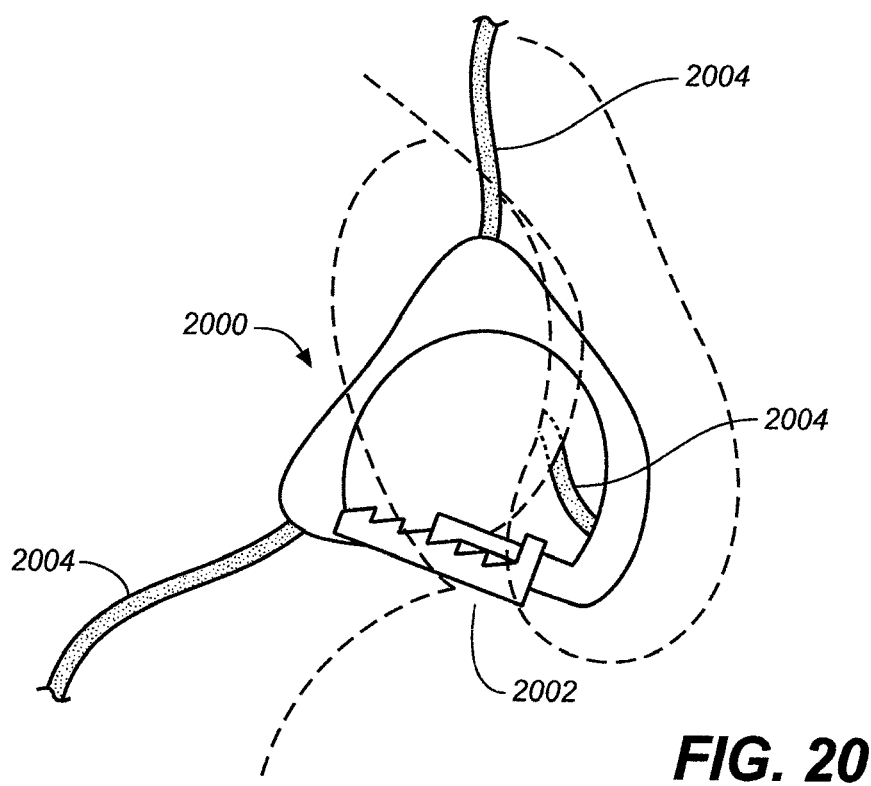
FIG. 20

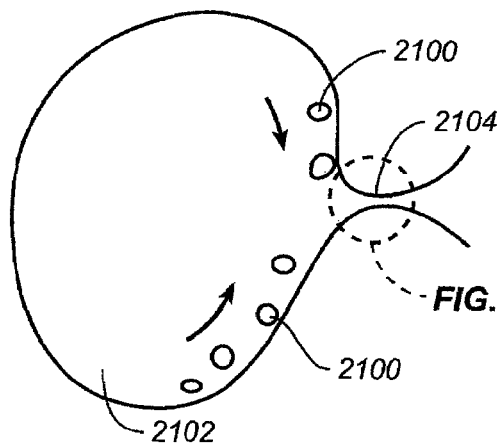 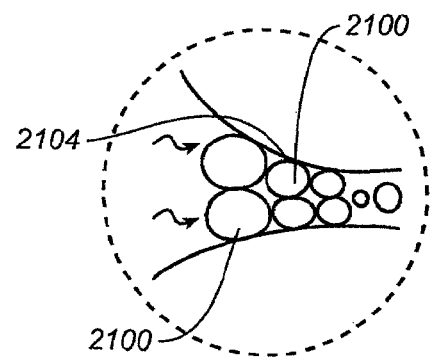
FIG. 21A  FIG. 21B
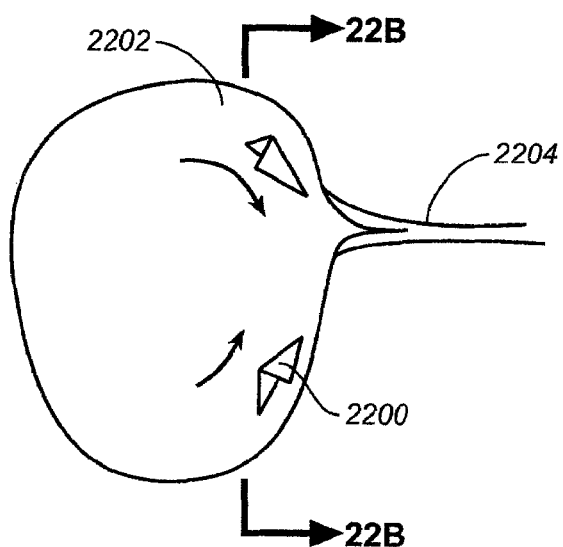 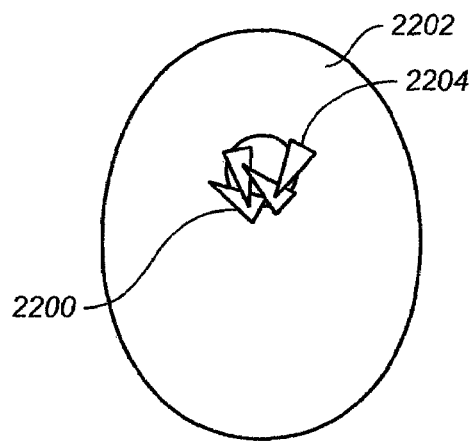
FIG. 22A  FIG. 22B

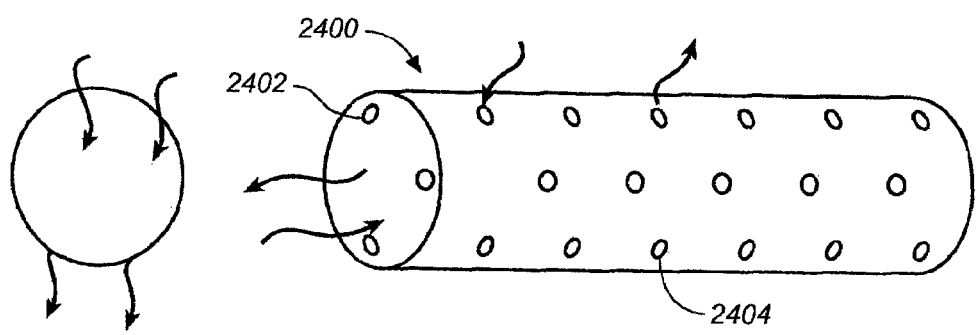
FIG. 23  FIG. 24
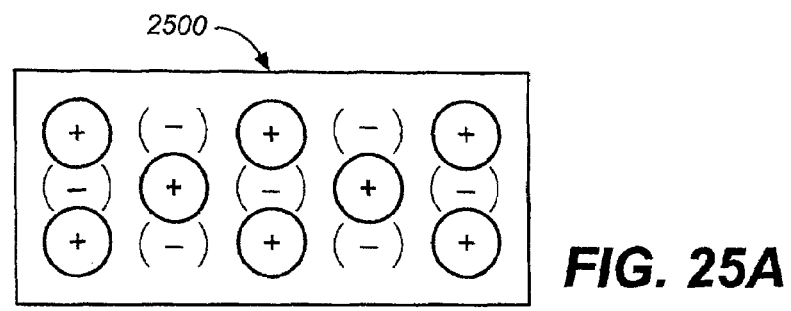
FIG. 25A
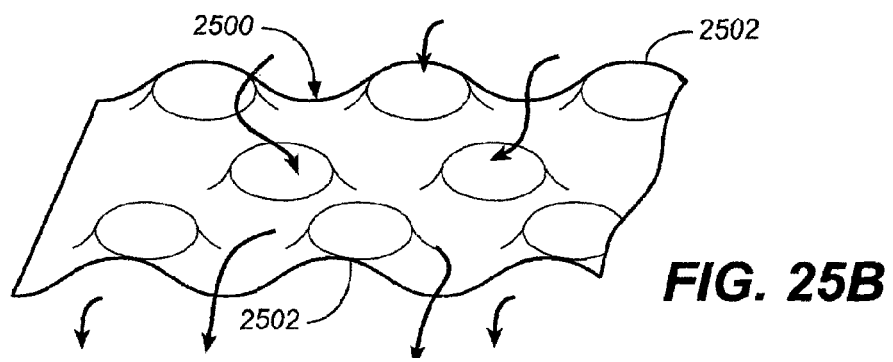
FIG. 25B

DEVICES AND METHODS FOR DELIVERING ACTIVE AGENTS TO THE OSTEOMEATAL COMPLEX

CROSS REFERENCE TO RELATED APPLICATIONS

This application is a continuation of, and claims the benefit of priority to, U.S. application Ser. No. 11/775,157, filed on Jul. 9, 2007, which application claims priority to U.S. Provisional Application Ser. No. 60/819,825, filed on Jul. 10, 2006, each of the above applications are hereby incorporated by reference in their entirety.

FIELD

The devices, methods, and kits described here are in the field of medical devices and local drug delivery to treat sinusitis and its related respiratory conditions. Specifically, the treatment of osteomeatal complex inflammation is described.

BACKGROUND

The osteomeatal complex (OMC) is a key area in the pathogenesis of sinusitis. The OMC includes the middle meatus and the narrow channels that provide the pathway for mucociliary clearance and ventilation of the anterior ethmoid, maxillary, and frontal sinuses. Thus, relatively minor swelling in this area, such as that associated with upper respiratory tract infections or allergic rhinitis, may lead to obstruction of any one or combination of these sinus cavities. As a result of blockage in the OMC, sinusitis may develop due to the accumulation of mucus, inflammatory cells, and bacteria, presence of low oxygen tension, and impaired immune responses in the OMC and surrounding tissues.

Medical treatment regimens used for sinusitis may be used to treat OMC inflammation. Typical medical treatment regimes may include a combination of oral antibiotics, topical or oral decongestants, topical steroid nasal sprays or solutions, or injectable oral steroids such as prednisone. Systemic methods (e.g., oral and injectables) commonly have significant disadvantages relating to side effects from the exposure of the entire body to the effects of the active agent. Topical methods (e.g., nasal sprays and other solutions) commonly have disadvantages relating to the limited site availability of the active agents both nasally and at the inflamed OMC anatomy (typically less than a 30 percent nasal drug delivered dose efficiency, and presumably far less at the specific OMC anatomy) as well as a short drug residence time at the inflamed site due to the effect of mucociliary clearance (typically less than 30 minutes dose residence time within the nasal passage).

When medical therapy fails, surgical treatment such as functional endoscopic sinus surgery (FESS) may be an alternative. The goal of FESS, and of sinus surgery generally, is to improve the drainage of the sinuses by enlarging the ostia of the maxillary and frontal sinuses, and opening the ethmoid sinus area by removing the ethmoid air cells under direct visualization. However, surgery itself creates inflammation, which can lead to post-operative fibrosis, stenosis, and/or polyposis that frequently obstructs the newly opened sinuses, requiring the surgeon to reoperate to revise the ostia and insert stenting devices to keep sinus ostia patent. Even in the resected post-surgical anatomy, access to many of the inflamed regions of the OMC remains difficult.

Other methods of post-surgical adjunctive drug delivery have required endoscopic placement of various drug hydrated packing materials, typically resident for a week or less at a time, and presumably delivering drug for shorter periods than the packing material residence time as only an acute one-time instillation of active agents is possible (as described in Shikani, A H, Use of Antibiotics for Expansion of the Merocel Packing Following Endoscopic Sinus Surgery, *ENT Journal* 75 (8): 524-527 (1996)). Such approaches are unlikely to allow consistent or controllable sustained release of active agents. Still other described approaches involve acute endoscopic injection of active agent releasing depots, as in the intramuscular injection of steroids (e.g., triamcinolone acetonide suspensions such as Kenalog) into adjacent soft tissue. These approaches require invasive rather than topical methods (e.g., intramuscular injection at a site), and neither treat the OMC region directly (which is primarily thin tissue membranes over bony cavities not suitable for an intramuscular depot) nor treat without significant collateral systemic and adjacent tissue exposure and adverse effects (e.g., the use of Kenalog in the paranasal and sinus anatomy has been linked to both systemic adrenal suppression as well as cases of ipsilateral blindness, in many cases permanent).

Consequently, new devices, methods, and kits to locally administer and provide sustained release of active agents directed to the OMC for treating sinusitis and its related respiratory conditions are desirable.

SUMMARY

The devices, methods, and kits described here are generally used to treat patients with sinusitis and related respiratory conditions. The related respiratory condition typically treated is osteomeatal complex inflammation. As used herein, the phrases "osteomeatal complex inflammation" or "OMC inflammation" refer to any reaction of tissue within the osteomeatal complex and its constituent adjacent anatomy that involves the inflammatory response. The inflammation may be caused by processes such as allergy (hypersensitivity), bronchitis, asthma, injury to mucosa within the OMC due to, e.g., trauma; surgery; infection by bacteria, viruses, or fungi; chemicals or drugs; cystic fibrosis, and benign or malignant tumors.

The devices may be made from solid or semi-solid materials, or materials that take such a form at or soon after their placement at the intended anatomy, and are generally formed in such a way to locally deliver one or more active agents to the OMC. The devices may be made from a biodegradable polymer, a nonbiodegradable polymer, a metal, or a combination thereof. The active agents that may be delivered include, but are not limited to, anticholinergic agents, antihistamines, anti-infective agents, anti-inflammatory agents, antiscarring or antiproliferative agents, chemotherapeutic or antineoplastic agents, cytokines, decongestants, healing promotion agents and vitamins, hyperosmolar agents, immunomodulator or immunosuppressive agents, leukotriene modifiers, mucolytics, narcotic analgesics, small molecules, tyrosine kinase inhibitors, peptides, proteins, nucleic acids, vasoconstrictors, and combinations thereof. In one variation, the active agent may be included in the biodegradable polymer or in a coating on the device. In another variation, the active agent may be encapsulated in microspheres or other micro-particles that are components of the device.

In addition to the drug delivery function described above, the devices may optionally perform one or more mechanical functions and may also have features configured to enhance their utility. Optional mechanical functions may include the stabilization of the natural or post-surgical anatomy, piercing and/or cannulation providing access conduits to, from and within the OMC anatomy and the sinuses, prevention of tissue adhesions as a physical adhesion barrier, coating and/or tissue separating spacer, and the replacement of natural anatomical features removed by surgery or disease processes. The devices described here may have features configured to be actively fixed to one or more tissues of the OMC or be passively placed or expanded within the OMC, and may be configured to either maintain their position within the OMC or to maintain contact with at least some of the various parts of the OMC anatomy using these features or other material properties such as mucoadhesion. Other devices may have features adapted to fill the space or maintain a separation between various parts of the OMC anatomy, e.g., between the uncinate process and middle turbinate, between the ethmoid bulla and the middle turbinate or between the lateral nasal wall and the middle turbinate. The devices may optionally include a portion that extends and delivers an active agent into a sinus ostium, a sinus cavity, and/or the nasal passage. If included, the active agent delivered to the sinus ostium, sinus cavity, and/or the nasal passage may be the same or different from the active agent delivered to the osteomeatal complex. The optional portion itself that extends into the sinus ostium, sinus cavity, and/or nasal passage may also be configured to have a function other than drug delivery, e.g., stabilization or lateralization of the middle turbinate, cannulation of the ostium or sinus cavity, etc. The devices may also change their insertion configuration and deploy through expansion, deformation or self-assembly into their final intended configuration after their placement. Kits may also be formed by packaging a device with one or more delivery conduits, insertion devices, or deployment devices, or by packaging together with one or more of various types of devices including functions supporting or enabling the access, placement, adjustment, expansion or deployment, and removal of device(s).

The described devices may be useful in surgical, non-surgical, and other therapeutic interventions related to the OMC to restore anatomical function and treat sinusitis and related respiratory conditions. Accordingly, the devices may be used to support sinus and nasal surgery, reduce the need for surgical revision, and/or prevent, delay, or reduce recurrence of sinusitis and related respiratory conditions.

BRIEF DESCRIPTION OF THE DRAWINGS

FIG. 4A is a perspective view of the clip. FIG. 4B is a cross-sectional view of the clip of FIG. 4A within the OMC anatomy. FIG. 4C shows an endoscopic view of the clip of FIG. 4A within the OMC anatomy.

FIG. 5A is a perspective view of the clip. FIG. 5B shows and endoscopic view of the clip of 5A within the OMC anatomy.

FIG. 6A is a perspective view of one end of the clip. FIG. 6B is an endoscopic view of the clip of FIG. 6A within the OMC anatomy.

FIG. 9A shows a compressive locking mechanism and FIG. 9B depicts an expansive locking mechanism.

FIGS. 11A-11E show multiple views of a micro-cannula for piercing and/or cannulating the OMC. FIG. 11A is a perspective view; FIG. 11B a frontal view; FIG. 11C an end view; FIG. 11D a side view; and FIG. 11E a side cross-sectional view.

FIGS. 12A-12E show multiple views of a micro-needle for piercing and/or cannulating the OMC. FIG. 12A is a perspective view; FIG. 12B is a frontal view; FIG. 12C is an end view; FIG. 12D is a side view; and FIG. 12E is a side cross-sectional view.

FIGS. 12F-12H are perspective views of the various tip configuration that may be used with the micro-needle of FIG. 12A.

FIGS. 13A-13E show multiple views of a staple for piercing tissues of the OMC. FIG. 13A is a perspective view; FIG. 13B is a frontal view; FIG. 13C is an end view; and FIG. 13D is a side view. In FIG. 13E, barb-shaped staple ends are shown.

FIGS. 14A-14F show multiple views of a locking deformation device for piercing and/or cannulating the OMC. FIG. 14A is a perspective view; FIG. 14B is a frontal view; FIG. 14C is an end view; FIG. 14D is a side view; FIG. 14E is a side cross-sectional view; and FIG. 14F shows the locking deformation rod of FIG. 14A within the OMC anatomy.

FIG. 15A is a side cross-sectional view of the device upon initial insertion within the OMC anatomy and FIGS. 15B-15C show locking of the device within the OMC anatomy.

FIG. 19 shows a perspective view of a device having an optional portion extending into a sinus cavity that anchors the device within the sinus cavity.

FIG. 20 shows a perspective view of a device having a plurality of optional pliable strands that extend into sinus cavities.

FIGS. 21A-21B illustrate cannulation of a sinus ostia using a self-assembling device in the form of beads.

FIGS. 22A-22B illustrate another variation of a self-assembling device in the form of triangular foils.

FIGS. 23, 24, and 25A-25B show various flow through features that may included in the described devices. FIG. 23 shows a porous bead; FIG. 24 a cylindrical device with a plurality of end and side apertures; and FIGS. 25A-25B an egg carton-like surface design.

FIG. 28A shows a two loop clip; FIG. 28B shows a three loop clip; FIG. 28C shows a four loop clip with a focused center; and FIG. 28D depicts a four loop clip with a spaced center.

DETAILED DESCRIPTION

The devices, methods, and kits described herein relate to the delivery of active agent(s) to the OMC to treat OMC inflammation. The OMC includes the middle meatus and the area adjacent to and including the narrow channels that provide mucociliary clearance and ventilation of the anterior ethmoid, maxillary, and frontal sinuses. As used herein, the terms "osteomeatal complex" or "OMC" refer to the anatomical space bounded laterally by the nasal wall, the lateral surface of the ethmoid bulla and anterior ethmoid cells, medially by the lateral surface of the middle turbinate, superiorly by (and including) the frontal recess up to the frontal sinus ostia, inferiorly by the superior surface of the inferior turbinate, posteriorly by the termination of the infundibular groove and the junction of the anterior surface of the basal lamella with the anterior ethmoid cells, and anteriorly by the anterior side of the uncinate process (which is also included in its entirety). If the ethmoid cells and bulla have been resected, then the OMC is bounded laterally by the nasal wall and medially by the lateral surface of the remnant middle turbinate. If the middle turbinate has also been resected, then the OMC is bounded medially by the nasal septum. If the uncinate process has been resected, then the OMC is bounded anteriorly by the anterior edge of the middle turbinate.

Figure 1A:
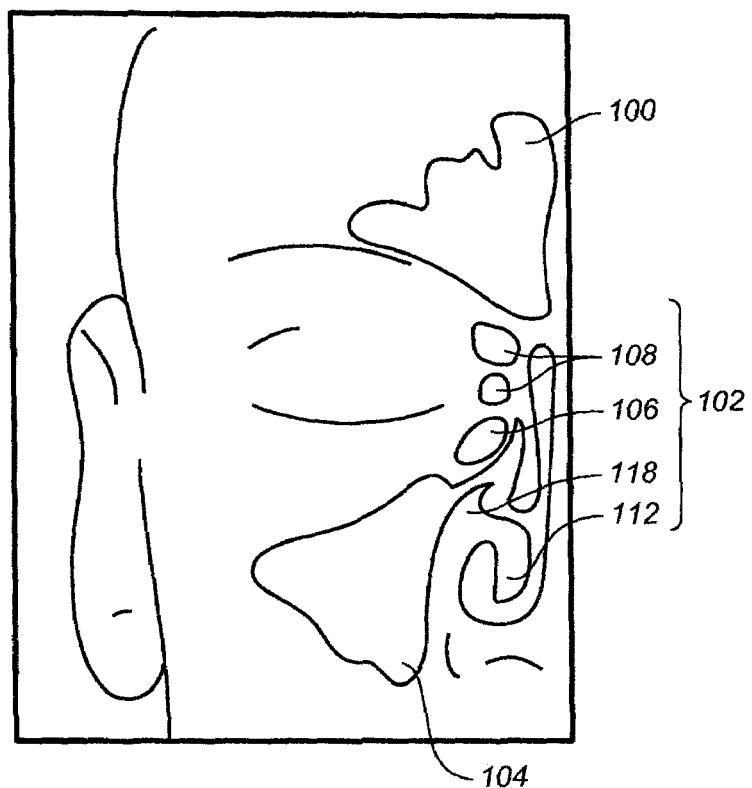
FIGS. 1A-1E show cross-sectional views of pre-surgical (FESS) sinus and OMC anatomy.
Figure 1B:
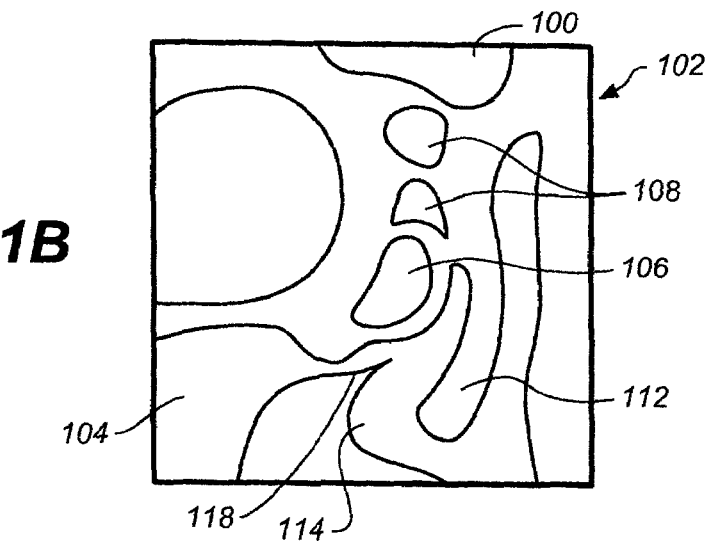
Figure 1C:
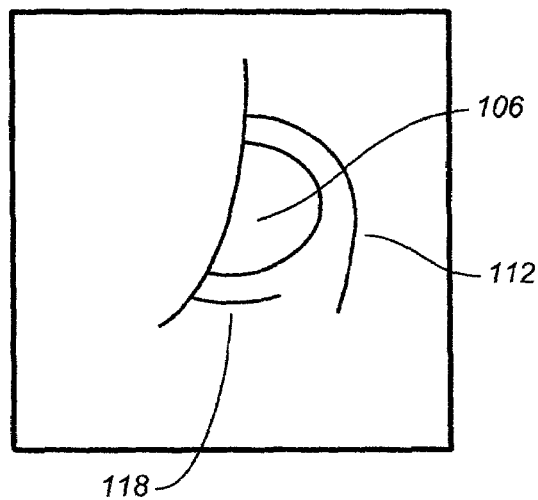
Figure 1D:
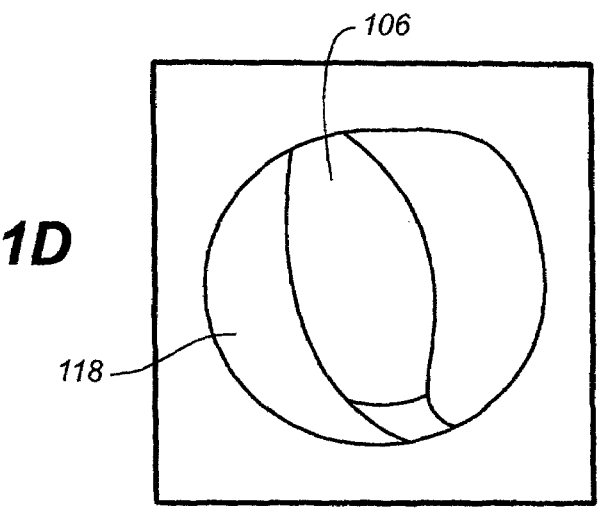
Figure 1E:
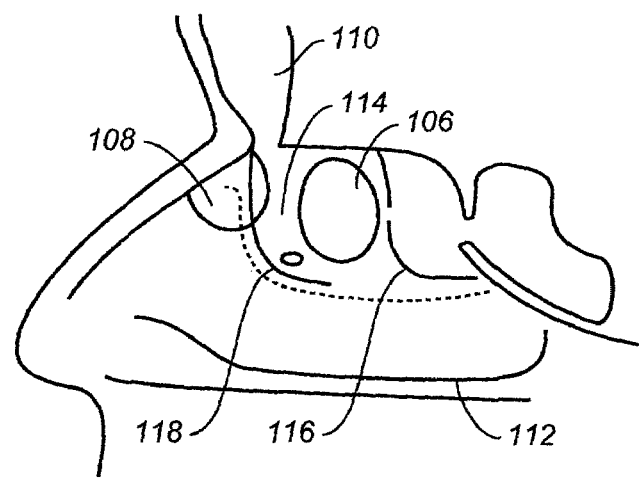

Shown in FIGS. 1A-1E are pre-surgical (FESS) views of the sinus anatomy. Specifically, FIG. 1A depicts a coronal sinus view of the pre-surgical sinus anatomy, FIG. 1B is an exploded coronal view of the OMC, FIG. 1C is a schematic view of the OMC, FIG. 1D is an endoscopic view of the OMC, and FIG. 1E is a sagittal view of the sinus OMC.

Specifically, shown in FIG. 1A, is frontal sinus (100), OMC (102), and the maxillary sinus (104). FIG. 1B is a partial exploded coronal view of the OMC (102). As noted above, pre-surgically (when neither the middle turbinate or uncinate process has been resected) the OMC refers to the anatomical space bounded laterally by the nasal wall and the lateral surface of the ethmoid bulla (106) and anterior ethmoid cells (108), medially by the lateral surface of the middle turbinate, superiorly by (and including), the frontal recess (110) up to the frontal sinus ostia, inferiorly by the superior surface of the inferior turbinate (112), posteriorly by the termination of the infundibular groove (114) and the junction of the anterior surface of the basal lamella (116) with the anterior ethmoid cells (108), and anteriorly by the anterior side of the uncinate process (118).

Figure 2:
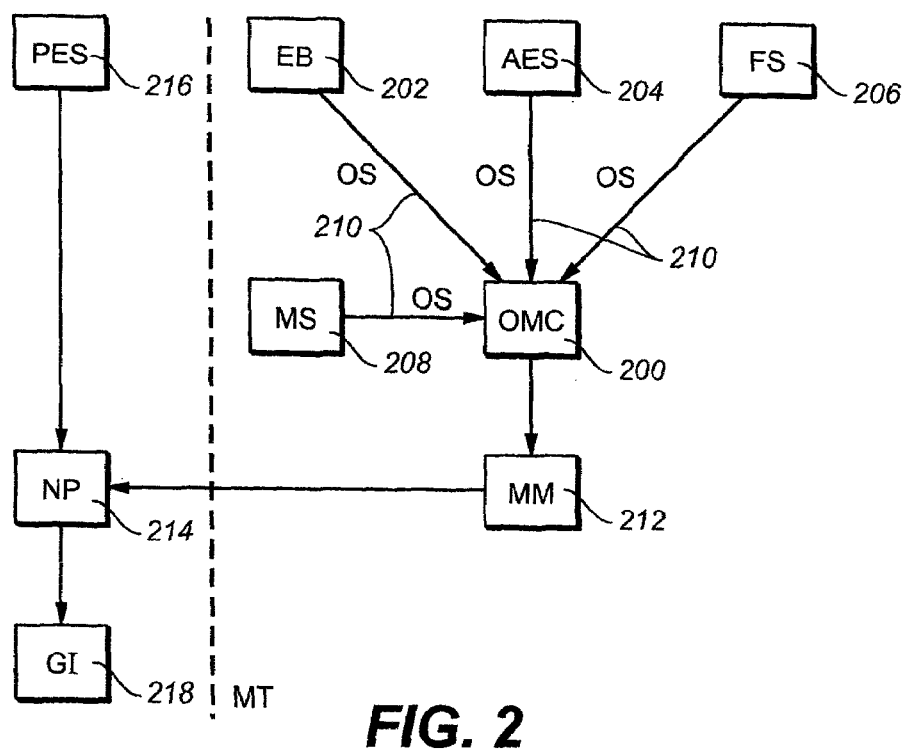
FIG. 2 is a flowchart showing mucociliary flow into and out of the OMC.

FIG. 2 is a flowchart illustrating the mucociliary flow into and out of the OMC (200). Specifically, mucus flows from the ethmoid bulla (202), the anterior ethmoid cells (204), frontal sinus (206), and maxillary sinus (208) to enter the OMC through their respective ostia (210). Mucociliary flow out of the OMC enters the middle meatus (212), which in turn enters the nasal passage (214). Flow from the posterior ethmoid cells (216) also enters the nasal passage (214). From the nasal passage, mucus then enters the gastrointestinal tract (218) via the nasopharynx, pharynx, hypopharynx, and esophagus.

Figure 3:
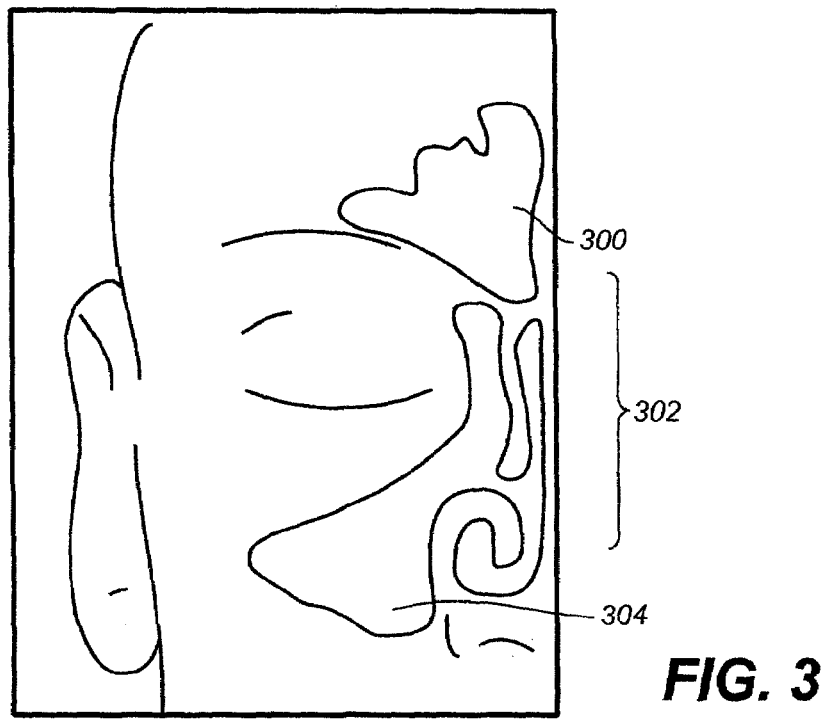
FIG. 3 illustrates a cross-sectional view of post-surgical (FESS) sinus and OMC anatomy.

FIG. 3 provides a coronal view of post-surgical (FESS) sinus anatomy. Shown there is frontal sinus (300), post-surgical OMC (302), and maxillary sinus (304). As noted above, if the middle turbinate has been resected, then the OMC is bounded medially by the nasal septum. If the uncinate process has been resected, then the OMC is bounded anteriorly by the anterior edge of the middle turbinate.

I. Devices

Described here are devices for treating sinusitis and its related respiratory conditions. In general, the devices comprise a therapeutically effective amount of an active agent, which is delivered for local sustained release to the OMC (including its adjacent anatomy). The related respiratory condition may be selected from the group consisting, without limitation of the foregoing, of inflammation of the OMC, OMC or sinus cavity inflammation due to surgery, including functional endoscopic sinus surgery (FESS); respiratory infections; sinusitis (acute or chronic); rhinitis; allergic rhinitis; rhinosinusitis (acute or chronic); upper respiratory tract infections; otitis media; bronchitis; bronchiolitis; asthma; tonsillitis and other chronic diseases of the tonsils and adenoids; laryngitis; tracheitis; nasal and sinus polyposis; neoplasms of the large and small airways; and nasal, sinus, and nasopharynx tumors.

The devices may be of any dimension, and as further described below, may be formed to be solid, semi-solid, biodegradable, nonbiodegradable, mucoadhesive, expansive, porous or flow-through, etc. The devices, or any part of the devices, may include, but are not limited to gels, foams, linear filaments, fibers, strands, ribbons, capillaries, tubes, woven and non-woven meshes or scaffolds, sheets, microspheres, microparticles, microcapsules, nanospheres, nanocapsules, nanoparticles (e.g., porous silicone nanoparticles), hydrophobic drug particles and the like, in situ gelling formulations, in situ bolus forming compositions, patches, films, micro-tablets, liquid filled capsules, liposomes and other lipid based compositions and the like (e.g., solid lipid nanoparticles), PEGylated compounds and the like, hydrogel formulations, emulsions, microemulsions, suspensions, or any other suitable drug-delivery formulation. Gels as used herein refer to any colloidal system in which a porous network of small micro- or nano-particles, which may or may not be themselves connected, span the volume of a liquid medium. In general, gels are apparently solid, jelly-like materials. Both by weight and volume, when exposed to an excess of the liquid medium, gels are or become mostly liquid in composition and thus exhibit densities similar to liquids, however have the structural coherence of solids. Gels include aerogels, where the liquid component of the gel has been replaced with a gas, and which are often otherwise classified as foams or nanofoams. Foams, including aerogels or nanofoams, are substances which are formed by trapping many gas bubbles in a liquid or solid, and thus can also be considered a type of colloid. Fibers as used herein consist of any continuous filament or other discrete elongated piece, which may be produced using various processes (e.g., extrusion, spinning, casting, spinning, cutting or slicing), and in turn may be combined into other structures, such as when spun into filaments, thread, string or rope, and when such are used as a component of composite materials, when matted into sheets or felts, when knitted or woven into meshes or fabrics, amongst others.

The devices may optionally serve mechanical functions such as stabilizing the natural or post-surgical anatomy, piercing or cannulating (e.g., providing access and potentially conduits to, from, and within the OMC anatomy and the sinuses), preventing tissue adhesions (e.g., by acting as a physical barrier or coating or as a tissue separating spacer), and replacing or substituting for natural anatomical features removed by surgery or disease processes. The devices may have optional portions that extend and deliver an active agent to the sinus ostium, a sinus cavity, and/or the nasal passage, which portion(s) may have a function other than drug delivery (e.g., including preventing or reducing stenosis of a sinus ostium by mechanical mechanisms). The devices may have features which provide for their fixation to any part of the OMC anatomy, for their deployment, expansion or deformation, and self-assembly into an intended configuration, as well as the locking or stabilization of that configuration, as further described in the below examples. In addition to those devices and features described below, the devices may comprise those devices (or portions thereof) described in Applicants' copending U.S. patent application Ser. No. 11/398, 342, filed on Apr. 4, 2006 and entitled "Device and Methods for Treating Paranasal Sinus Conditions," which is hereby incorporated by reference in its entirety. In these variations, the devices would be sized and shaped to fit within the OMC anatomy as described below.

Active and Passive Fixation

The devices may be configured for active or passive fixation, which may be useful in positioning, deploying, and anchoring the devices to any part of the OMC anatomy. As used herein, the phrases "active fixation," "actively fixing," and the like refer to devices and methods that visually alter the OMC anatomy in some fashion (e.g., puncturing, piercing, clamping, stimulating tissue ingrowth, and the like). Similarly, the phrases "passive fixation," or "passively fixing" and the like refer to devices and methods that do not visually alter the OMC anatomy (e.g., space filling, space fitting, friction fitting, tension fitting, mucoadhesion, etc.). Of course, a device configured for passive fixation may become an active fixation device if it begins to visibly alter the OMC anatomy. It should also be understood that devices may be configured for both active and passive fixation. For example, a device may comprise one portion designed to pierce an area of the OMC anatomy (active portion) and another portion designed to expand to fill some portion of the OMC anatomy (passive portion).

The devices may include one or more elements that help to actively fix it to the sinus mucosa. For example, as shown in FIGS. 16A-16L, the active fixation elements may be one or more spikes (16A), arrows (16B), opposed spikes (16C), barbs (16D), hooks (16E), triangular ridges (16F), screws (16G), springs (16H), and the like. In addition to being triangular in geometry, the ridges may also be formed to be round (16I), square (16J), directionally orientated or deployed (16K which can be inserted as a flat ridge and deploys directionally upon pulling the device backwards or proximally against the direction of insertion), concave (as in 16L, but also including other variations of the previous designs where concave versions of the aforementioned convex and protruding shapes might provide active fixation attributes through encouraging ingrowth, or alternatively, through passive fixation mechanisms), and the like. Furthermore, combinations of any number or all of the aforementioned active and passive fixation elements may also be used in the same devices. As previously noted, the devices may be of any dimension, and the above fixation techniques extend to microstructured and microparticle devices such as that formed by extrusion, molding, casting, and lithography techniques.

Clips

Figure 4A:
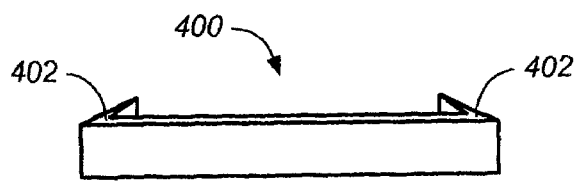
FIGS. 4A-4C show multiple views of an OMC clip having two tension members.
Figure 4B:
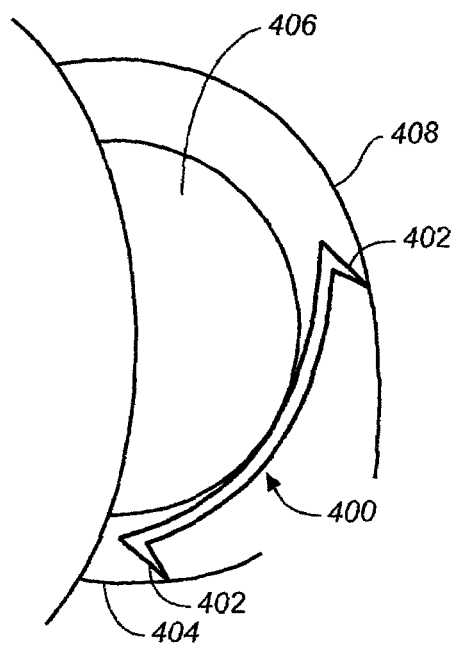
Figure 4C:
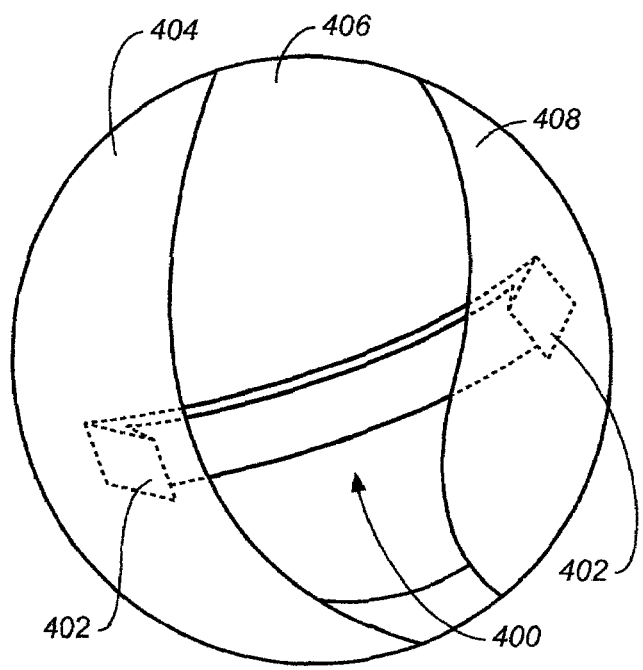
Figure 4D:
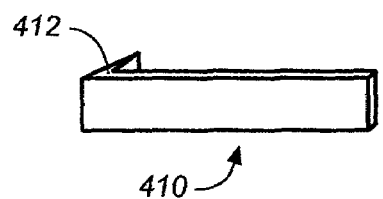
FIG. 4D is a perspective view of an OMC clip having one tension member.

Devices may be fashioned into clips, which generically are any structure designed for holding itself to or down against the sinus mucosa, or for holding any section of anatomy into a desired position (e.g., as in supporting the middle turbinate). FIGS. 4A and 4D provide illustrative clips that may be used with the methods described herein. For example, shown in FIG. 4A is a perspective view of clip (400) having two tension members (402). FIG. 4B is a schematic representation of clip (400) positioned in the OMC. As shown there tension members (402) are tensioned against the uncinate process (404) and middle turbinate (408) respectively. This is shown endoscopically in FIG. 4C where clip (400) is shown traversing the uncinate process (404) and middle turbinate (408). While the clip shown here is configured for placement between the uncinate process and the middle turbinate, such need not be the case. For example, the device can be configured for placement between any of the uncinate process, the ethmoid bulla, the middle turbinate, and the nasal wall. For example, the device may be configured to be placed between the uncinate process and the middle turbinate, the ethmoid bulla and the middle turbinate, the uncinate process and the ethmoid bulla, and the middle turbinate and the nasal wall. FIG. 4D shows a perspective view of clip (410) having only a single tension member (412). While the tension members shown in FIGS. 4A and 4D are shown having a similar geometry, angular in nature, the tension members may be of any appropriate geometry that allows the clip to have sufficient tension to be held in place. Similarly, while clips (400) and (410) are depicted as passive fixation devices, they need not be. Indeed, they may be modified to include an active fixation element as described above that may pierce, puncture, depress, or otherwise alter the anatomy of the OMC. For example, tension members (402) and (412) can be configured to have sharp edges, or to be self-piercing in nature. Similarly, while the clips shown have members which are generally rectangular in nature, any suitable clip geometry may be used. Such devices may include various transverse profiles for their members (e.g., round, oval, wing-like, triangular, square, rectangular, and the like), which may be formed into fibers, strands, sheets, struts, woven or non-woven mesh, or plate structures.

Figure 5A:
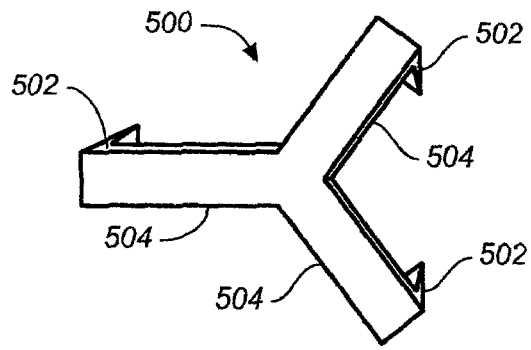
FIGS. 5A-5B show a "Y" shaped OMC clip.
Figure 5B:
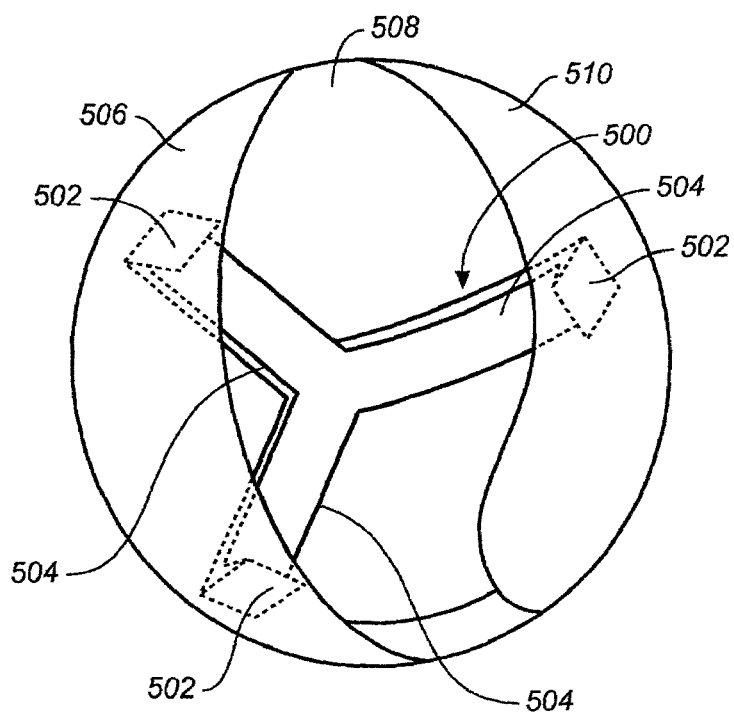
Figure 6A:
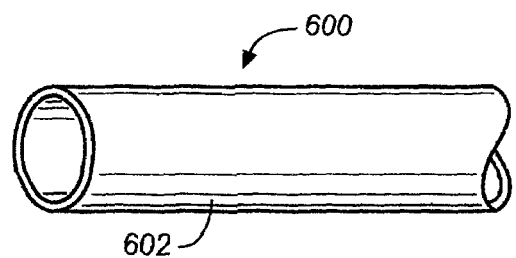
FIGS. 6A-6B depict a tubular OMC clip.
Figure 6B:
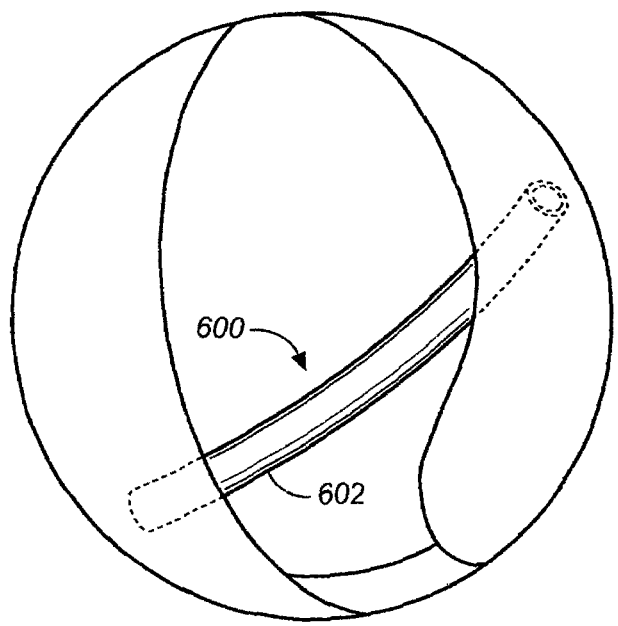
Figure 6C:
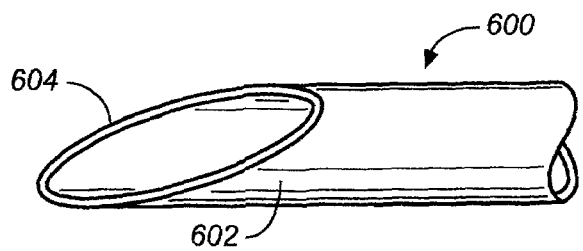
FIG. 6C shows the clip of FIG. 6A with a sharp tip.

FIG. 5A shows another variation of a suitable clip (500), which is generally "Y" shaped in nature. In this variation, clip (500) has three extension members (504) terminating in three tension members (502). FIG. 5B shows an endoscopic view of the device when placed in the OMC. Similar to the device placement shown in FIG. 4C, clip (500) is configured for placement between uncinate process (506) and middle turbinate (510), traversing ethmoid bulla (508). Again, the clips described here may be of any suitable geometry, and may be configured for active or passive fixation. While clip (500) is shown with three extension members, any number of extension members may be used as practicable. Similarly, the clips may be configured to not have any tension members, as shown in FIGS. 6A-6C. Shown there is a tubular clip (600), where the clip body (602) is configured to apply the appropriate tension to keep it in place. FIG. 6B shows an endoscopic view of clip placement, and FIG. 6C shows one variation where the tubular clip has been configured for active fixation by way of a sharp tip (604) located at the end of clip body (602). It should be understood that the clip without tension members need not be tubular, and that the tubular clip shown in FIGS. 6A-6C is simply an illustrative example of devices that may used in accordance with the methods described herein. Similarly, any of the clips described herein may be configured to have an expansive force (e.g., the passive fixation devices) or compressive force (e.g., the active fixation devices), which would either help push the extension member(s) outward or inward as the case may be, helping to secure it within the OMC anatomy.

Figure 10:
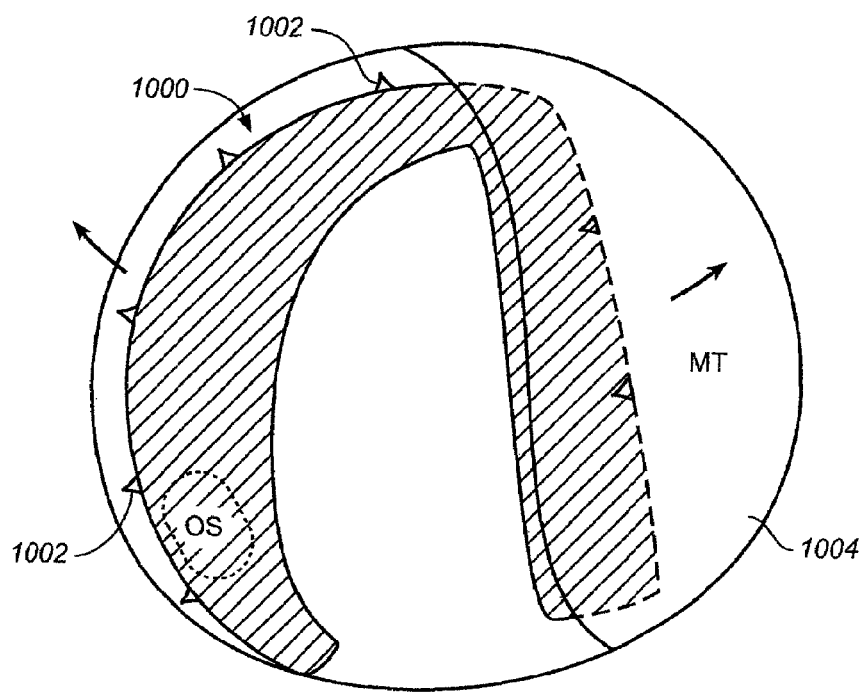
FIG. 10 shows a perspective view of another variation of an osteomeatal clip within the OMC anatomy, for particular use after functional endoscopic sinus surgery.

FIG. 10 shows an illustrative clip (1000) for a post-surgical procedure. As shown there, the clip (1000) has a series of barbs (1002) or other active fixation elements for actively securing the clip to the post-surgical anatomy, in this instance to the middle turbinate (1004). This device may also be helpful in stabilizing the middle turbinate, and preventing its lateralization and adhesion formation with the lateral nasal wall, or in acting as a replacement of some of the mechanical functions of a partially or fully resected post-surgical uncinate process.

Figure 28A:
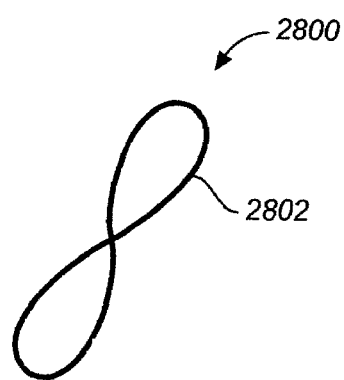
FIGS. 28A-28D show another variation of an OMC clip.
Figure 28B:
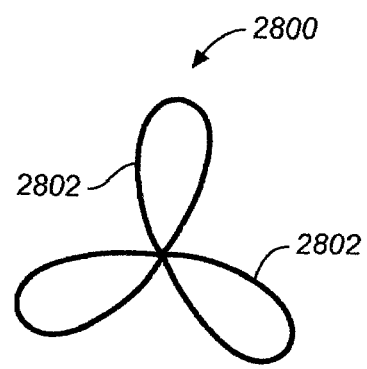
Figure 28C:
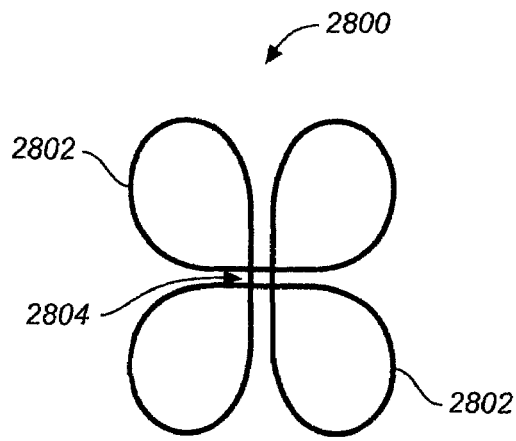
Figure 28D:
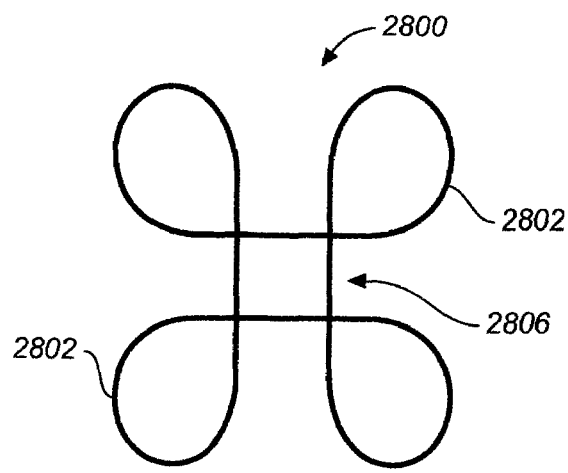
Figure 28E:
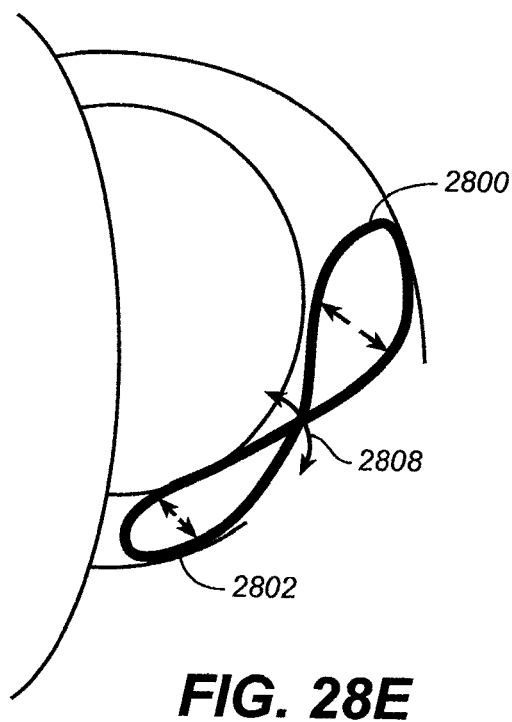
FIG. 28E shows a cross-sectional view of the clip of FIG. 28A within the OMC anatomy.
Figure 28F:
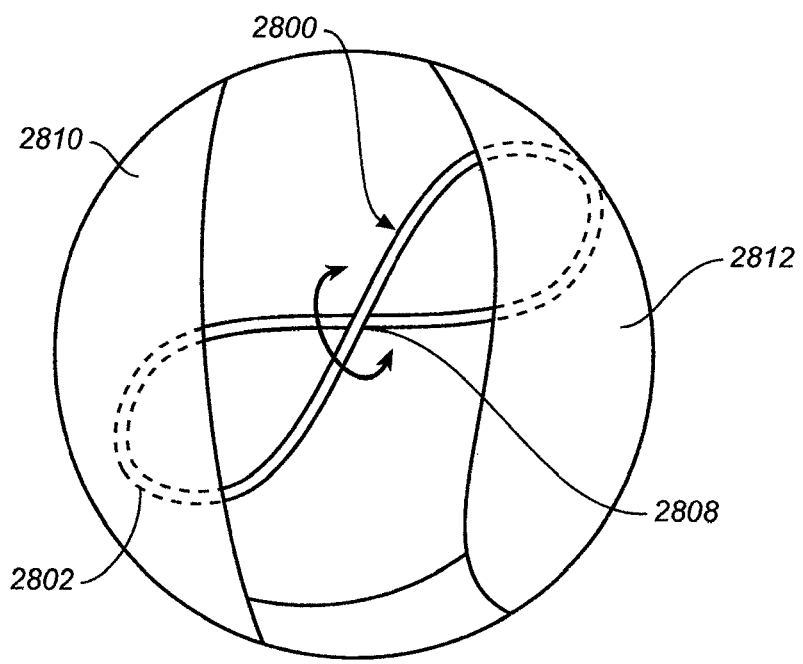
FIG. 28F shows an endoscopic view of the clip of FIG. 28A within the OMC anatomy.

FIGS. 28A-28D show another variation of a suitable clip (2800), which is made from a looped fiber or strip. The fiber or strip may be of any profile, e.g., flat or round. The clips may be configured to have any number of loops (2802). The clip has two loops (2802) in FIG. 28A, three loops (2802) in FIG. 28B, and four loops (2802) in FIGS. 28C-28D. In addition, the four loop clip may be configured to have a focused center (2804), as illustrated in FIG. 28C, or a spaced center (2806), as shown in FIG. 28D. Perspective and endoscopic views of the clip of FIG. 28A are shown in FIGS. 28E and 28F respectively. For example, FIG. 28E shows a clip (2800) having two loops (2802) within the OMC anatomy. There may be expansive tension between the sides of the loops to help passively fix the clip in place as shown by the arrows. The device may also rotate or twist about its center point (2808) as shown by the arrow. FIG. 28F shows the clip (2800) traversing and tensioned against, the uncinate process (2810) and middle turbinate (2812).

Figure 29:
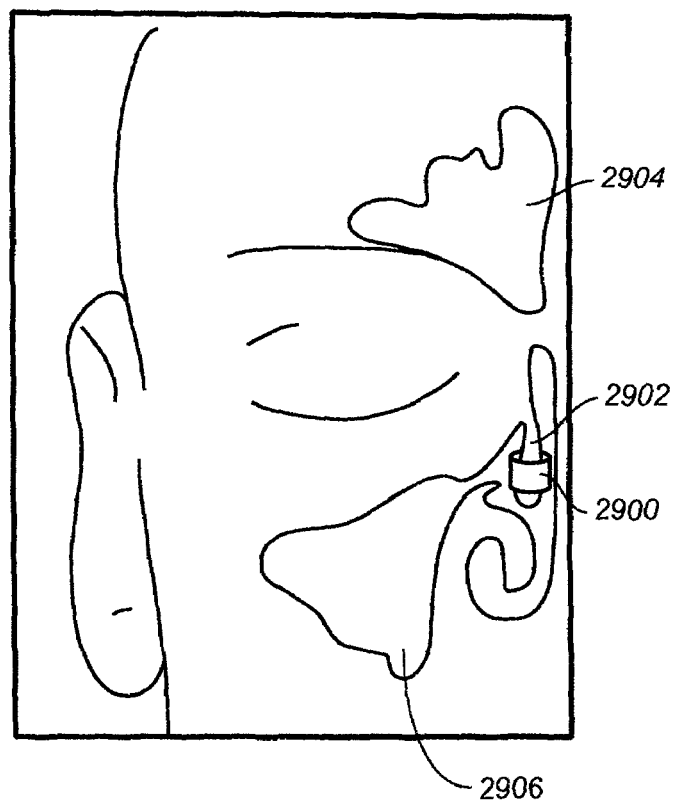
FIG. 29 shows a cross-sectional view on an illustrative clip within the OMC anatomy, and specifically, on the middle turbinate.

FIG. 29 shows another variation of a clip, where the clip is attached directly to the middle turbinate. As shown there, clip (2900) surrounds and grips in a clamping fashion middle turbinate (2902). Frontal (2904) and maxillary sinuses (2906) are shown for reference. While the clip shown in FIG. 29 is shown as a simple cylindrical device, any suitable clip geometry may be used (e.g., "C-shaped" or "U-shaped," etc.). In some variations, having a "C-shaped" or "U-shaped" device (i.e., having an open slot or slit) may be desirable to aid in slipping the clip onto the turbinate from either the side of the turbinate or from beneath the turbinate. It should be understood that the clip need not fully wrap around the turbinate like a band. The clip may have any number or combination of passive or active fixation elements and any number or combination of flow through elements (e.g., holes, slots, etc.).

Coils

Figure 7:
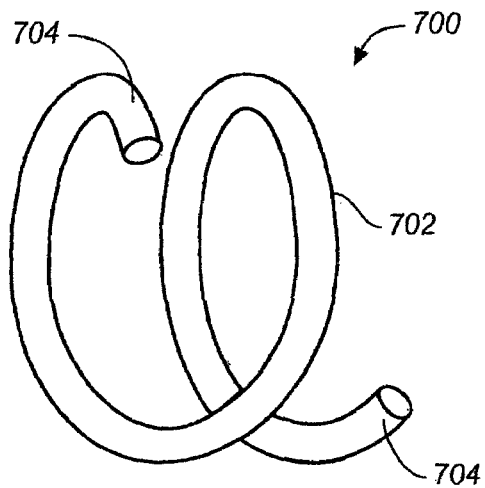
FIG. 7 shows a perspective view of an OMC coil.
Figure 8A:
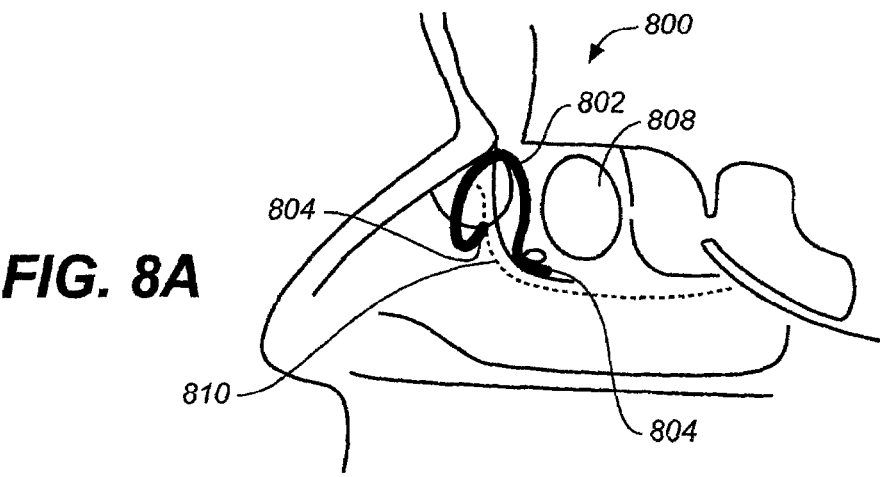
FIGS. 8A-8B show the coil of FIG. 7 placed within the OMC anatomy.
Figure 8B:
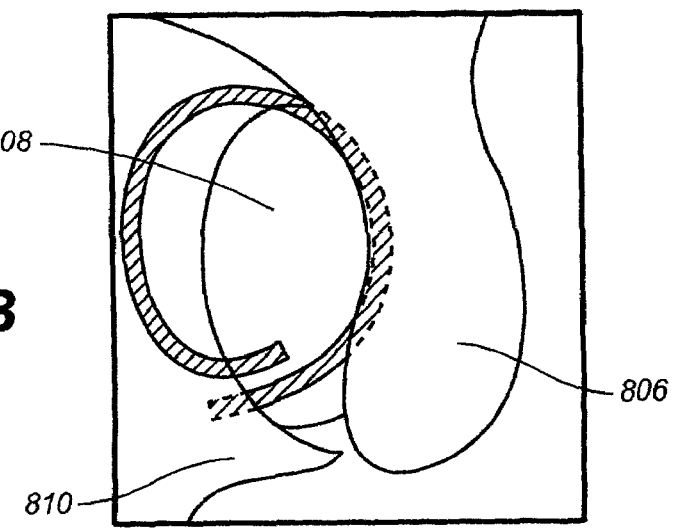

Devices may also be fashioned into coils, which generically are a series of loops. Coils may be fashioned into a spiral or helical shape, amongst other shapes, or otherwise formed by winding a fiber against a support in their manufacture or fabrication. FIG. 7 shows another device that may be used to treat OMC inflammation. Shown there is coil (700), having turns (702) and tension members (704). The coil may have any number of suitable turns (702). As with the clips described above, the device may be configured for active or passive fixation (e.g., by altering the tension members to make their ends sharp, etc., or by altering the device body, e.g., by including barbs, etc.). FIGS. 8A and 8B show the coil of FIG. 7 placed in the OMC anatomy. As shown in these figures, one tension member (804) is between the middle turbinate (806) and the ethmoid bulla (808), while the other tension member (804) is between the ethmoid bulla (808) and the uncinate process (810), the coil looping at turn (802).

Figure 9A:
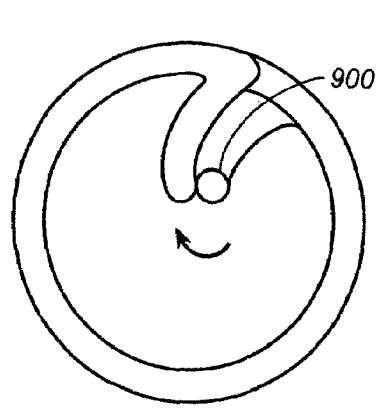
FIGS. 9A-9B show end views of locking mechanisms that may be employed with the coil of FIG. 7.
Figure 9B:
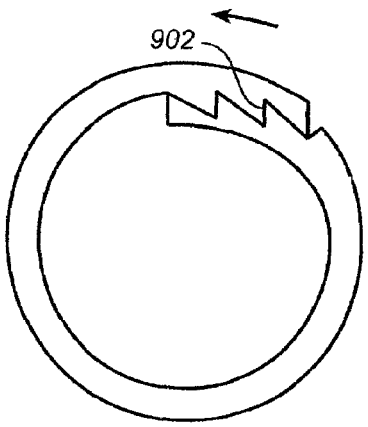

The coils described here may further comprise a lock or a locking mechanism as shown, for example, in FIGS. 9A and 9B. Shown in FIG. 9A is a compressive locking mechanism (900). The compressive locking mechanism (900) comprises a spring catch, so that when a compressive force is applied to the spring, the ends of the spring catch. FIG. 9B is a depiction of an expansive locking mechanism (902). Expansive locking mechanism (902) comprises a series of teeth. Any number of suitable teeth may be used. When expansive force is applied to the spring, the teeth of the locking mechanism prevent the spring from fully opening. Other locking features may be used as described below.

Piercing and Cannulation

Devices that can pierce and/or cannulate the anatomy of the OMC are also described here. These devices may be configured for placement on or within the uncinate process, on or within the ethmoid bulla, on or within the anterior ethmoid cells, or on or within the middle turbinate.

FIG. 11A is a perspective view of a micro-cannula (1100) configured for piercing a portion of the OMC anatomy. FIG. 11B shows a frontal view of the micro-cannula (1100) of FIG. 11A, while FIG. 11C shows an end view of the micro-cannula (1100). FIGS. 11D and 11E show side and cross-sectional side views of micro-cannula (1100) respectively. As shown in these figures, micro-cannula (1100) may include a plurality of openings (1102) within its distal portion (1104) that connect with space (1106) and lumen (1108). Although space (1106) is not shown as communicating with the tip (1110) of the micro-cannula, it can be designed as such if desired.

FIG. 12A is a perspective view of a micro-needle (1200). FIG. 12B is a front view of micro-needle (1200) and FIG. 12C is an end view. Similarly, FIGS. 12D and 12E are side and cross-sectional side views of the micro-needle respectively. The micro-needle can be of any gauge and designed with or without a lumen. The distal tip (1202) of the micro-needle may be of any configuration as deemed necessary. For example, distal tip (1202) may configured as an arrow (FIG. 12F), barb (FIG. 12G), star (FIG. 12H), and the like.

FIG. 13A shows a perspective view of a staple (1300), while FIGS. 13B and 13C show frontal and end views respectively. FIG. 13D shows a top view of the staple (1300). Staple (1300) may be of any size and shape, depending on such factors as desired area of implantation, type of material made from, surgeon preference, etc. Staple ends (1302) and piercing members may also be of various configurations. For example, as shown in FIG. 13E, staple ends (1302) may include barbs (1304). Staples may also be made of memory materials, or combinations of various materials effecting a shape memory or mucoadhesive effect further securing the staple ends and piercing members.

While certain devices have been described, it should be understood that they are merely illustrative variations. Indeed, any device configured to pierce or cannulate a portion of the OMC anatomy may be suitable for use with the methods described herein. For example, the portion of the device configured to pierce (e.g., the device tip) may have a variety of configurations, e.g., the portion can have one piercing edge or two piercing edges. Furthermore, the devices may be formed to locally or systemically release active agents themselves (e.g., be constructed of drug releasing materials, or including drug releasing components or coatings, such as biodegradable polymers) over a period of time, or be configured as conduits through which active agents may be delivered.

Locking or Deformation

The devices may utilize alternative locking or deformation features, in addition to those previously disclosed for coils with respect to FIGS. 9A and 9B, in order to stabilize or fix a device in a desirable configuration or anatomical position or to provide another mechanical function such as cannulation. One piercing and cannulation device variation with a locking feature is shown in FIGS. 14A-14F. Shown in FIG. 14A is a locking-deformation rod (1400). FIGS. 14B and 14C are frontal and end views of locking deformation rod (1400) respectively. FIGS. 14D and 14E are side and cross-sectional side views respectively. FIG. 14F shows an illustrative method of inserting the device in the OMC anatomy. As shown there in FIG. 14F the deformation rod (1400) is moved distally into and through the OMC anatomy (1402), and then pulled proximally back so that distal tip (1404) of deformation rod (1400) deforms, thereby locking the device in place.

Figure 15A:
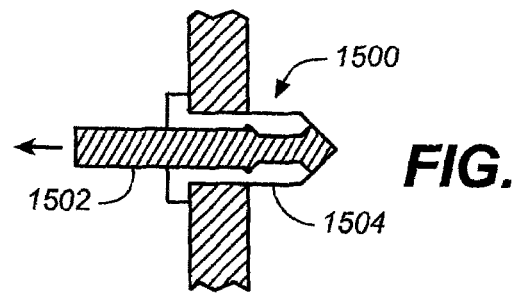
FIGS. 15A-15C show multiple views of another variation of a locking deformation device for piercing and/or cannulating the OMC.
Figure 15B:
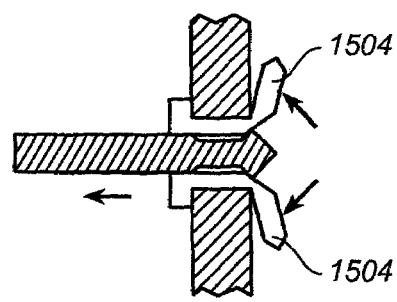
Figure 15C:
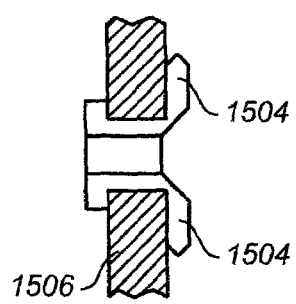
Figure 16A:
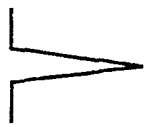
FIGS. 16A-16H show perspective views of various active fixation elements.
Figure 16B:
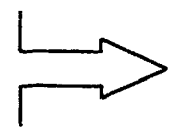
Figure 16C:
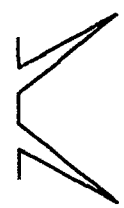
Figure 16D:
Figure 16E:
Figure 16F:
Figure 16G:
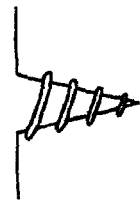
Figure 16H:
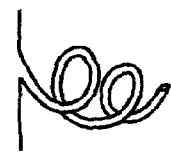
Figure 16I:
FIGS. 16I-16L show cross-sectional views of various ridge configurations.
Figure 16J:
Figure 16K:
Figure 16L:

FIGS. 15A-15C show another variation of a locking deformation member (1500). As shown in FIG. 15A, locking deformation member (1500) comprises slidable rod (1502) and locking ends (1504). As slidable rod (1502) is pulled proximally within locking deformation member (1500), locking ends (1504) are outwardly deformed, locking the member (1500) in place within OMC anatomy (1506). In the variation shown, slidable rod (1502) may be removed only subsequent to deformation of the deformation member (1500), exposing a new lumen conduit and cannulation port through the OMC anatomy in the process.

Several alternative mechanical locking mechanisms may be used. Examples comprise tightening screw sleeves, opposing directional ridges, concentric tubes and interior friction (including where tapering or ridged tubes are used), rotating asymmetric interior members creating frictional opposition when locked (as with rotating oval cylinders within the lumen of a surrounding round or oval member), protuberances extending from the interior or through the exterior of a device (as through portal windows) when locked, or individual member deformation (e.g., through tension, expansion or with compression), and the like. Such locking mechanisms may reversibly or irreversibly hold the device in the intended configuration or position.

Device Extension Outside of the OMC

Figure 17:
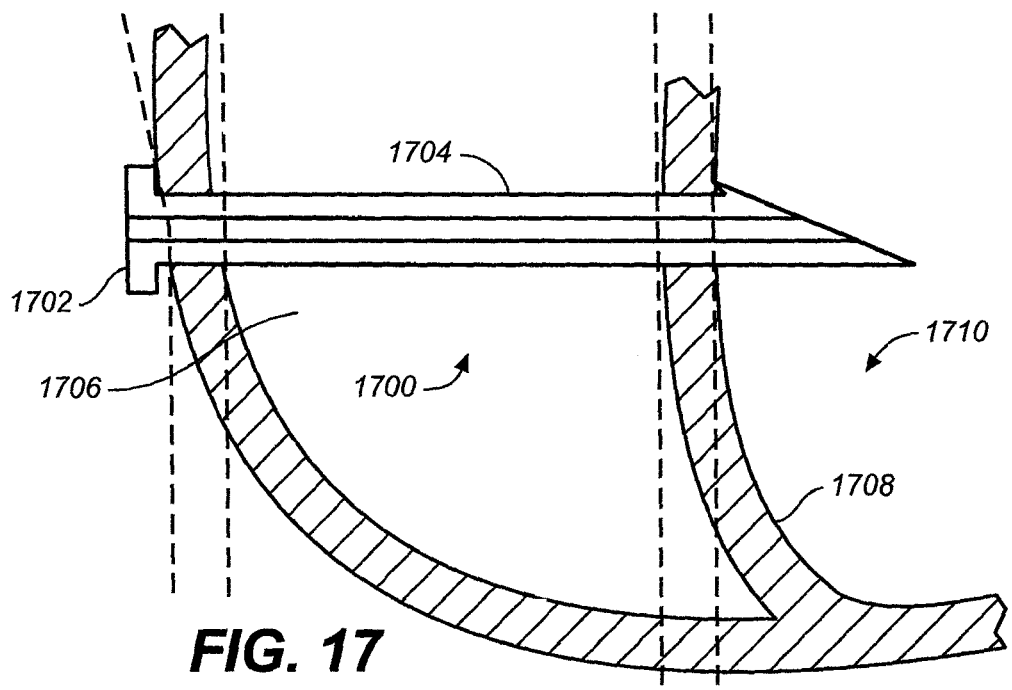
FIG. 17 depicts a cross-sectional view of a device having an optional portion extending within multiple ethmoid air cells.
Figure 18:
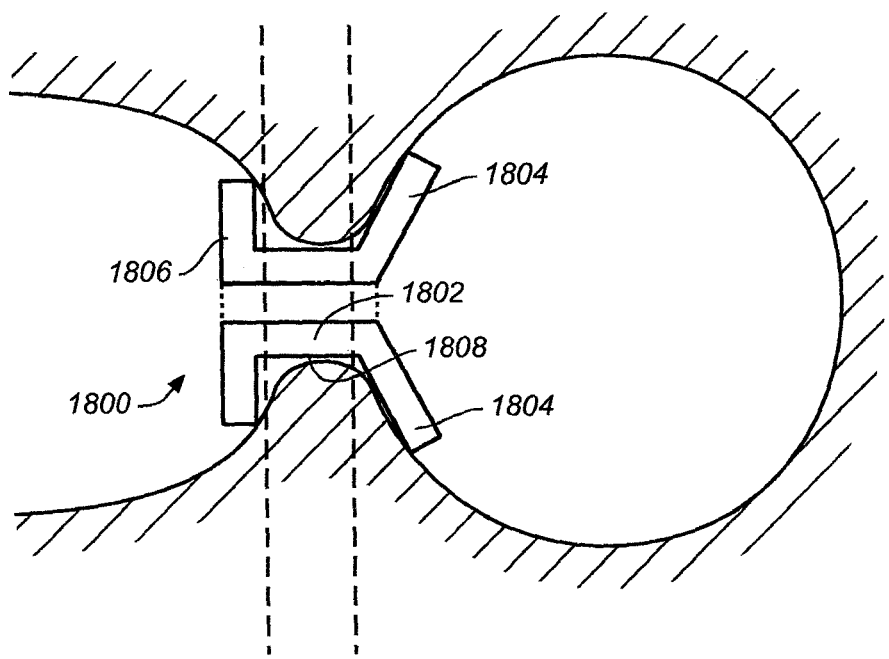
FIG. 18 illustrates a cross-sectional view of another device having an optional portion extending into the maxillary sinus cavity.

The devices may be designed to optionally include a portion or member that resides within a sinus ostia, a sinus cavity, the nasal passageway, and/or other areas beyond boundaries of the OMC. For example, as shown in FIG. 17, device (1700) may have an OMC portion (1702) and a sinus portion (1704) that extends into one or more sinus cavities. In FIG. 17, device (1700) pierces and cannulates the ethmoid bulla (1706) and septum (1708) between the ethmoid bulla (1706) and anterior ethmoid cell (1710) to create accessory openings for mucus drainage. In another variation, as shown in FIG. 18, a locking deformation device, according to the previous description in FIGS. 15A-15C, is shown after its deployment (deformation) through a natural or surgically operated upon sinus ostium, and subsequent to the removal of the slideable rod member, exposing a lumen in the remaining deformation member. So deployed, the locking deformation device (1800) includes an ostial portion (1802) and locking ends (1804) as the sinus portion (1804) that extend from OMC portion (1806). In this instance, ostial portion (1802) lies within natural ostium (1808). In a further variation, the sinus portion may comprise an anchoring member that keeps the device fixed within the OMC. For example, FIG. 19 shows a device (1900) having first end (1902) within the OMC and second end (1904) threaded through sinus ostium (1906) into maxillary sinus (1908). As the device (1900) is pulled out of maxillary sinus (1908), second end (1904) is configured to radially expand such that it anchors second end (1904) within maxillary sinus (1908). In yet another variation, the optional portion may include drug-eluting pliable strands or cannulating tubes (that may or may not be perforated). For example, as shown in FIG. 20, device (2000) with expansive locking mechanism (2002) comprises a plurality of pliable drug-eluting strands (2004) configured to extend into sinus ostia, sinus cavities, and/or associated infundibulums (e.g., the ethmoid infundibulum) or recesses. It should be understood that the extension portions or members described in FIGS. 17-20 are simply illustrative examples of extension portions or members that may be used in accordance with the methods described herein, and that extension portions or members of any configuration may be employed.

Self-Assembly

The devices may be configured to self-assemble within a sinus cavity, creating a larger intended configuration from a plurality of smaller component parts, which may or may not be symmetrical or uniform in their design. The larger assembled configuration may comprise, as shown in FIG. 21A, beads (2100) of various sizes that have been placed into a sinus cavity (2102), e.g., by injection, cannulation, lavage, Proetz procedure, or other placement techniques, and move toward the natural ostium (2104) via normal mucociliary transport. FIG. 21B is an expanded view of the beads (2100) within sinus ostium (2104). As the beads pass through the ostium (2104), the larger beads are detained to gradually cannulate the ostium, with mucociliary clearance possible both around and through gaps among the deposited beads (as described below, also within the beads as porous beads may also be used). The smaller beads are released as the ostium reopens.

Self-assembling devices may also be configured from asymmetric shapes such as triangular foils. As shown in FIG. 22A, triangular foils (2200) placed within a sinus cavity (2202) migrate toward the natural ostium (2204) due to normal mucociliary clearance. FIG. 22B is an end view of the ostium from within the sinus cavity that shows how triangular foils (2200) cluster at the ostium (2204), but due to their particular geometry are almost always capable of allowing flow therethrough. Other examples of symmetrical and asymmetrical forms amenable to such applications include microspheres, loops, rings, corrugated strips and tubes, among others, all of which may self-assemble and interlock without occlusion or prevention of mucociliary clearance.

Figure 26:
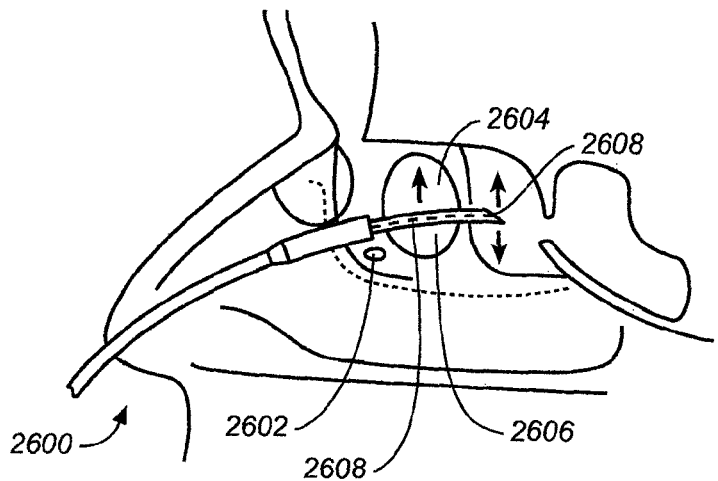
FIG. 26 depicts one variation of a device for delivery of the self-assembling devices of FIGS. 21A-21B and FIGS. 22A-22B.

The self-assembling devices may be introduced into the sinuses using various conduits, e.g., catheters, including steerable catheters, angiocatheters, needles, and the like. The conduits may include a distal aperture and/or a plurality of side apertures for delivery of the self-assembling devices into the sinus cavity. For example, as shown in FIG. 26, conduit (2600) is advanced through the nasal passage and uncinate process (2602) into ethmoid air cells (2604). The distal end (2606) of the conduit comprises a plurality of side apertures (2608). Once within the ethmoid air cells (2604), the self-assembling devices may be administered through the side apertures (2610) of the conduit into ethmoid air cells (2604) using a syringe, push rod, pressurized gas, or other technique well known in the art. The devices may also be placed within the sinus cavity using the Proetz procedure.

Porosity and Flow-Through

The devices may be configured to include various features that allow continued mucociliary clearance or features that promote flow of mucus through and/or around them. For example, as shown in FIG. 23, the device may comprise one or more porous beads (2300) that permit mucus flow therethrough, as shown by the arrows. The device may also be formed as perforated structures (e.g., holes, slots, etc.). Shown in FIG. 24 is a cylindrical device (2400) having a plurality of end apertures (2402) and side apertures (2404) interconnected by channels (not shown). As shown by the direction of the arrows, mucus may flow into a side aperture (2402) and out an end aperture (2402) and vice versa. In another variation, as shown in FIGS. 25A and 25B, the surface of the device may be textured to comprise a series of concavities 2500 (indicated by (−) in FIG. 25A) and convexities 2502 (indicated by (+) in FIG. 25A) such that mucus flows through the depressions formed by the concavities, as shown by the arrows in FIG. 25B. Other suitable structures for flow-through and continued mucociliary clearance include, but are not limited to, gels, sponges, porous monoliths, woven and nonwoven meshes, and the like. Illustrative, but non-limiting examples of suitable porosity and flow-through materials for use with the methods and devices provided here are described generally, or conceptually, in the following references: Sarkar et al. Development and Characterization of a Porous Micro-patterned Scaffold for Vascular Tissue Engineering Applications. *Biomaterials* 27: 4775-4782 (2006); Rezwan et al. Biodegradable and Bioactive Porous Polymer/inorganic Composite Scaffolds for Bone Tissue Engineering. *Biomaterials* 27: 3413-3431 (2006); Svec F, Porous Monoliths. *Recent Developments in LC Column Technology* June: 2-6 (2003); Landgraf et al. Polymer Microcarrier Exhibiting Zero-Order Release. *Drug Delivery Technology* 3(1): 1-12 (2003); Lu et al. In vitro and in vivo degradation of Porous Poly(DL-lactic-co-glycolic acid) Foams. *Biomaterials* 21:1837-1845 (2000); Mooney et al. Novel Approach to Fabricate Porous Sponges of Poly(D,L-lactice-co-gylcolic acid) Without the use of Organic Solvents. *Biomaterials* 17:1417-1422 (1996); and Benson J R. Highly Porous Polymers. *American Laboratory* April (2003).

Space-Filling and Expansion

Figure 27:
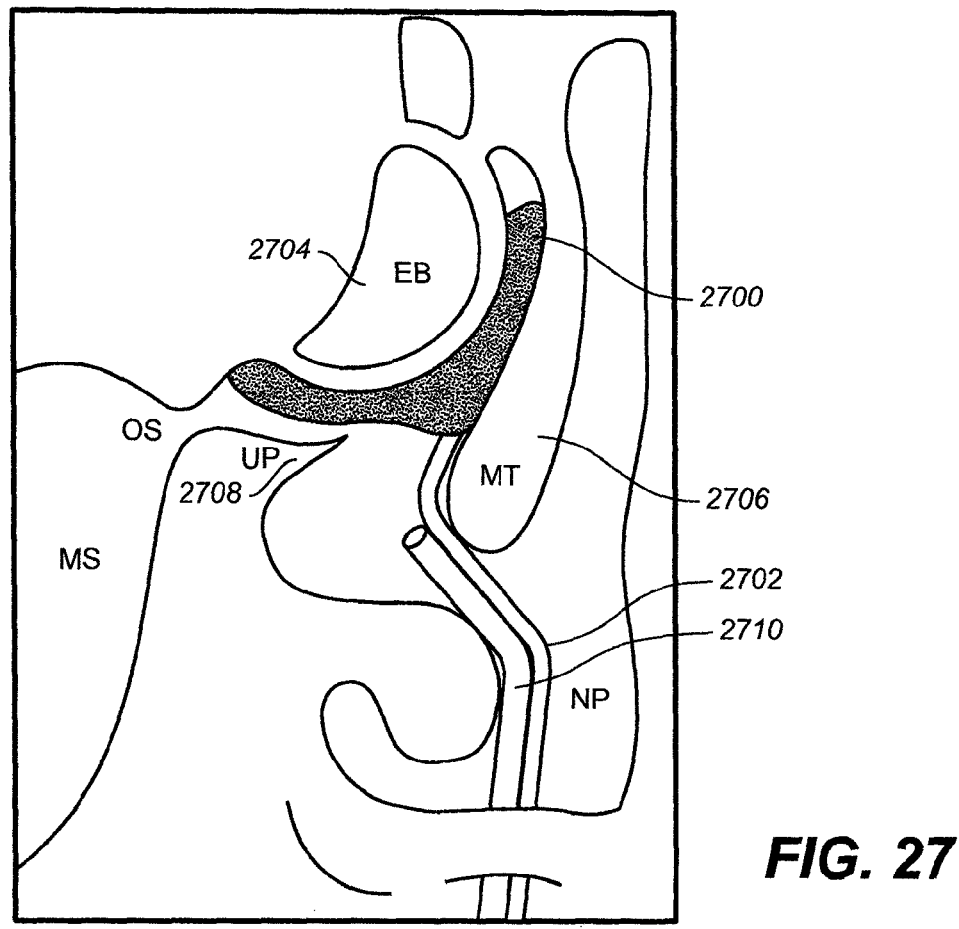
FIG. 27 shows a space filling device within the OMC anatomy.

The devices described here may also be adapted to fill the space between the uncinate process, the ethmoid bulla, the middle turbinate, the nasal wall, and any combination thereof. For example, the device can be adapted to fill the space between the uncinate process and the middle turbinate, the ethmoid bulla and the middle turbinate and/or the uncinate process. Suitable devices for space filling include, but are not limited to gels, foams, microspheres, microparticles, microcapsules, nanospheres, nanocapsules, nanoparticles (e.g., porous silicone nanoparticles or solid lipid nanoparticles), hydrophobic drug particles and the like, in situ gelling formulations, in situ bolus forming compositions, patches, films, micro-tablets, liquid filled capsules, liposomes and other lipid based compositions and the like, PEGylated compounds and the like, hydrogel formulations, emulsions or microemulsions, suspensions, or any other suitable drug-delivery formulation. For example, as shown in FIG. 27, space filling device (2700) is delivered via conduit (2702) to fill the space between the ethmoid bulla (2704), the middle turbinate (2706), and the uncinate process (2708). A visualization tool (2710), e.g., an endoscope, may be used to help deliver the device to the appropriate location within the OMC.

In addition to space filling upon placement of the devices, space filling may also be accomplished by the in-place expansion of the device dimensions after placement, either through use of materials that expand with hydration, through use of polymeric or non-polymeric shape memory materials, or though mechanical expansion, either reversibly, as in materials with elastomeric properties, or irreversibly, as in materials that might be plastically deformed. Illustrative, but non-limiting examples of suitable space-filling and expansion materials for use with the methods and devices provided here are described generally, or conceptually, in the following references: Hägerström H Polymer Gels as Pharmaceutical Dosage Forms. Dissertation for the Degree of Doctor of Philosophy (Faculty of Pharmacy) in Pharmaceutics. *Comprehensive Summaries of Uppsala Dissertations for the Faculty of Pharmacy* 293: 76 (2003); Guan et al. Fabrication of Polymeric Microparticles for Drug Delivery by Soft Lithography. *Biomaterials* 27:4034-4041 (2006); and Vila et al. PEG-PLA Nanoparticles as Carriers for Nasal Vaccine Delivery. *Journal of Aerosol Medicine* 17(2): 174-185 (2004). Some of the references identified just above in the porosity and flow-through section have equal applicability as well.

Active Agents

Any active agent may be included in the devices described herein so long as they are suitable to treat OMC inflammation or a related respiratory condition and are capable of achieving the desired release kinetics. Inflammation is used generically herein to describe the complex biological response of vascular and surrounding tissues to harmful stimuli, such as pathogens, damaged cells, pro-inflammatory disorders, or irritants, and includes both a protective and healing function. Treatment of inflammation as described herein may include the treatment of either the harmful stimuli (such as with antimicrobial active agents), treatment of the cellular (such as active agents acting on inflammatory cell recruitment and infiltration (e.g., neutrophils, eosinophils, amongst others) of tissue from the vasculature to the mucosal wall) and molecular inflammatory responses (such as active agents impacting cell receptor, signal transduction, nuclear factor signaling, nucleic acid transcription or transrepression, translation, post-translational modification, exudative cytokine release and extracellular signaling by affected and relevant cells), and treatment and aid of the healing response (such as active agents either through supporting cellular regeneration of the original cell type (e.g., active agents for angiogenesis and/or growth factors) or replacement of the injured tissue with scar tissue), as well as all acute, chronic, or traumatic manifestations thereof. Other active agents may be used to treat conditions or complications secondary to surgery, implantation of the devices, or other treatment, such as in post-surgical inflammation, inflammation due to foreign body reactions to the devices, and secondary infections or biofilm formation and microbial colonization of the devices themselves. In one variation, the active agent may be included in a coating on the device. In another variation, the active agent may be encapsulated in a microparticle (e.g., a hydrocolloid microparticle or a polymeric microparticle). The active agents that may be used in such a device include, but are not limited to, anticholinergic agents, antihistamines, anti-infective agents, anti-inflammatory agents, antiscarring or antiproliferative agents, chemotherapeutic/antineoplastic agents, cytokines such as interferon and interleukins, decongestants, healing promotion agents and vitamins (e.g., retinoic acid, vitamin A, dexapanthenol, vitamin B, and their derivatives), hyperosmolar agents, immunomodulator/immunosuppressive agents, leukotriene modifiers, mucolytics, narcotic analgesics, small molecules, tyrosine kinase inhibitors, peptides, proteins, nucleic acids, vasoconstrictors, or combinations thereof. Anti-sense nucleic acid oligomers or other direct transactivation and/or transrepression modifiers of mRNA expression, transcription, and protein production may also be used. Anti-infective agents generally include antibacterial agents, antifungal agents, antiparasitic agents, antiviral agents, and antiseptics. Anti-inflammatory agents generally include steroidal and nonsteroidal anti-inflammatory agents.

Examples of antibacterial agents that may be suitable for use with the described methods and devices include, but are not limited to, aminoglycosides, amphenicols, ansamycins, β-lactams, lincosamides, macrolides, nitrofurans, quinolones, sulfonamides, sulfones, tetracyclines, vancomycin, and any of their derivatives, or combinations thereof. In one variation, β-lactams are the preferred antibacterial agents.

β-lactams that may be suitable for use with the described methods and devices include, but are not limited to, carbacephems, carbapenems, cephalosporins, cephamycins, monobactams, oxacephems, penicillins, and any of their derivatives. In one variation, penicillins (and their corresponding salts) are the preferred β-lactams.

The penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, amoxicillin may be included in the paranasal sinus device. In another variation, the device includes ampicillin. Penicillins combined with clavulanic acid such as Augmentin® (amoxicillin and clavulanic acid) may also be used.

Examples of antifungal agents suitable for use with the described methods and devices include, but are not limited to, allylamines, imidazoles, polyenes, thiocarbamates, triazoles, and any of their derivatives. In one variation, imidazoles are the preferred antifungal agents. Antiparasitic agents that may be employed include such agents as atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N—,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-l]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents (e.g., silver chloride, silver oxide, silver nanoparticles).

Typically, if inclusion of an anti-inflammatory agent is desired, a steroidal anti-inflammatory agent, e.g., a corticosteroid, is employed. Exemplary steroidal anti-inflammatory agents include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In one variation, budesonide is included in the device as the steroidal anti-inflammatory agent. In another variation, the steroidal anti-inflammatory agent may be mometasone furoate. In yet another variation, the steroidal anti-inflammatory agent may be beclomethasone. In yet a further variation, the steroidal anti-inflammatory agent may be fluticasone propionate.

If a nonsteroidal anti-inflammatory agent is used, suitable agents include, but are not limited to, COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide).

The chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethimide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth- 1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, analogs/congeners, derivatives of such compounds, and combinations thereof.

Exemplary decongestants that may be incorporated in the OMC devices, include, but are not limited to, epinephrine, pseudoephedrine, oxymetazoline, phenylephrine, tetrahydrozolidine, and xylometazoline. Mucolytics that may be used include, but are not limited to, acetylcysteine, domase alpha, and guaifenesin. Anti-histamines such as azelastine, diphenhydramine, and loratidine may also be used.

In those instances where it is desirable to remove water from tissue, e.g., to remove fluid from polyps or edematous tissue, a hyperosmolar agent may be employed. Suitable hyperosmolar agents include, but are not limited to, furosemide, sodium chloride gel, or other salt preparations that draw water from tissue or substances that directly or indirectly change the osmolarity of the mucous layer.

Materials

When the devices are made with polymers, selection of the biodegradable or nonbiodegradable polymer to be employed will vary depending on the residence time and release kinetics desired, method of device delivery, particular therapeutic agent used, and the like. In all instances, the biodegradable polymer when degraded results in physiologically acceptable degradation products.

Suitable biodegradable and biocompatible polymers for use in making the OMC devices include, but are not limited to, polymers such as a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof. Biodegradable shape memory polymers, such as those commercialized by nmemoScience in Aachen, Germany, or those described in U.S. Pat. Nos. 5,189,110 or U.S. Pat. No. 5,139,832, may also be employed, as may shape memory configurations of the aforementioned co-polymers using multiple layers or adjacent coatings of differing co-polymers (as described in Venkatraman S S et al. Biodegradable Stents with Elastic Memory. *Biomaterials* 27: 1573-1578 (2006)). See also, Zheng et al. Shape Memory Properties of poly(D,L-lactide)/hydroxyapatite composites. *Biomaterials* 27: 4288-4295 (2006).

As used herein, a poly(lactide); a poly(glycolide); a poly (lactide-co-glycolide); a poly(lactic acid); a poly(glycolic acid); a poly(lactic acid-co-glycolic acid) will all be referred to as PLG, PLG polymers, or lactide/glycolide polymers. Lactide/glycolide polymers for the drug delivery devices and compositions of this invention are typically made by melt polymerization through the ring opening of lactide and glycolide monomers. Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. In one variation, linear lactide/glycolide polymers are used; however, star polymers may be used as well. In other variations, high molecular weight polymers may be used to form the devices of this invention, for example, to meet strength requirements and extend bioabsorption time. In other instances, low molecular weight polymers may be used when resorption time and not material strength is important. The lactide portion of the polymer has an asymmetric carbon. Racemic DL-, L-, and D-polymers are commercially available to include in the devices of this invention. The L-polymers are more crystalline and resorb slower than DL-polymers. In addition to copolymers comprising glycolide and DL-lactide or L-lactide, copolymers of L-lactide and DL-lactide are also commercially available. Additionally, homopolymers of lactide or glycolide are commercially available. Star polymers of lactide or glycolide or lactide/glycolide copolymers are also commercially available.

In the case when the biodegradable polymer is poly(lactide-co-glycolide), poly(lactide), or poly(glycolide), the amount of lactide and/or glycolide in the polymer may vary. In one variation, the biodegradable polymer contains from about 0 to about 100 mole %, from about 40 to about 100 mole %, from about 50 to about 100 mole %, from about 60 to about 100 mole %, from about 70 to about 100 mole %, or from about 80 to about 100 mole % lactide, and from about 0 to about 100 mole %, from about 0 to about 60 mole %, from about 10 to about 40 mole %, from about 20 to about 40 mole %, or from about 30 to about 40 mole % glycolide, wherein the amount of lactide and glycolide is 100 mole %. In other variations, the biodegradable polymer may be poly(lactide), about 85:15 poly(lactide-co-glycolide), about 75:25 poly (lactide-co-glycolide), about 65:35 poly(lactide-co-glycolide), or about 50:50 poly(lactide-co-glycolide), where the ratios are mole ratios. When the biodegradable polymers are fibers, they may be made via an extrusion process. For example, the polymer may be extruded via a melt phase process to form a fiber with a suitable diameter. The fiber can than be further drawn down to smaller diameters, if desirable. The extrusion temperature will typically be above the melt temperature of the polymer, and will vary depending on the type of polymer chosen. The drawing process will typically involve drawing the polymer at a temperature above the glass transition temperature and then heat setting the polymer at a temperature between the glass transition temperature and the melting temperature. The fiber may be any suitable length. Fiber meshes may be formed by braiding or weaving, and the mesh density may be controlled with tension, needle space, fiber diameter, and the like. The fibers may also be coated (co-extruded, spray coated or dip (immersion, gap, curtain or otherwise) coated), as discussed in detail in several references incorporated herein.

In another variation, when the biodegradable polymer is poly(lactide-co-glycolide), poly(lactide), or poly(glycolide), the polymer has an intrinsic viscosity of from about 0.15 to about 1.5 dL/g, from about 0.25 to about 1.5 dL/g, from about 0.25 to about 1.0 dL/g, from about 0.25 to about 0.8 dL/g, from about 0.25 to about 0.6 dL/g, or from about 0.25 to about 0.4 dL/g as measured in chloroform at a concentration of 0.5 g/dL at 30° C. Various solvents, plasticizers, porosigens and other excipients may be added to the polymer in order to impact biodegradation and drug release rate. For factors affecting the degradation rate, see, e.g., Tracy et al. Factors Affecting the Degradation Rate of Poly(lactide-co-glycolide) Microspheres in vivo and in vitro. *Biomaterials* 20:1057-1062 (1999) and Wu X S and Wang N, Synthesis, Characterization, Biodegradation, and Drug Delivery Application of Biodegradable lactic/glycolic acid Polymers. Part II: Biodegradation. *J. Biomater. Sci. Polymer Edn.* 12(1):21-34 (2001).

If a nonbiodegradable polymer is used to make or incorporate into the device or composition, suitable nonbiodegradable polymers include, but are not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Furthermore, the devices, or any portion thereof, may be made from any biocompatible, biodegradable or nonbiodegradable polymer that is mucoadhesive. In some instances, the device may be coated with a mucoadhesive, which may or may not be a polymer (for example, solid and semi-solid materials, such as hydrogels, e.g., comprised for example of PLG polymers, polyacrylic acids (Noveon™, Carbopol™), carageenan, alginate, xantham gum, carboxymethylcellulose, hydroxypropyl cellulose, chitins, chitosan, hyaluronic acids, lectins and their derivatives). Several theories of the microscopic nature of mucoadhesion exist: the adsorption, diffusion, electronic, fracture and wetting theories all explain some of the desirable characteristics of a mucoadhesive material. Empirically, the strength of the mucoadhesiveness is related to biomaterial characteristics (type of formulation, hydration and swelling characteristics, molecular mass, concentration, and chemical structure including functional groups, charge, ionization, chain flexibility, crosslinking density and spatial orientation), environmental characteristics (hydration condition, swelling, environmental pH, contact time and applied pressure), and physiological characteristics (mucociliary clearance, mucus turnover, and disease states) as described in Ugwoke M I et al. The Biopharmaceutical Aspects of Nasal Mucoadhesive Drug Delivery. *Journal of Pharmacy and Pharmacology* 53: 3-22 (2001); Edsman K and Hägerström H. Pharmaceutical Applications of Mucoadhesion for the Non-Oral Routes. *Journal of Pharmacy and Pharmacology* 57: 3-22 (2005); Woodley J. Bioadhesion: New Possibilities for Drug Administration? *Clin Pharmacokinet* 40(2):77-84 (2001); Harikampakdee et al. Spray-dried Mucoadhesive Microspheres: Preparations and Transport Through Nasal Cell Monolayer. *AAPS PharmSciTech* 7(1): E1-10 (2006); Chowdary K P R and Rao Y S Mucoadhesive Microspheres for Controlled Drug Delivery. *Biol. Pharm. Bull.* 27(11):1717-1724 (2004); Gavini et al. Mucoashesive Microspheres for Nasal Administration of an Antiemetic Drug, Metoclopramide: in vitro/ex-vivo Studies. *Journal of Pharmacy and Pharmacology* 57: 287-294 (2005); Jain et al. Development and Characterization of Mucoadhesive Microspheres Bearing Salbutamol for Nasal Delivery. *Drug Delivery* 11:113-122 (2004); Peppas N A and Huang Y. Nanoscale Technology of Mucoadhesive Interactions. *Advanced Drug Delivery Reviews* 56:1675-1687 (2004); and Jasti et al. Recent Advances in Mucoadhesive Drug Delivery Systems. Business Briefing: Pharmatech (2003). The biomaterial chosen can often be optimized for the above characteristics, further enhancing mucoadhesion. For example, the mucoadhesive may absorb water to swell and become adhesive. The mucoadhesiveness and expansion of such a device can be used to facilitate fixation within the OMC. The devices may also be made from a polymer that carries a charge.

Mucoadhesive properties may also be imparted by the macroscopic mechanical construction of the devices, particularly the surface area to total mass (not average molecular weights) ratio for the device (or mucoadhesive portion thereof), and specifically the interfacial surface area (the area of the device that directly contacts the mucosa or is otherwise in contact with the fluid phase of the mucus) to total supported (by mucoadhesion) mass ratios. For a particular material, within a given set of biomaterial, environmental, and physiological characteristics, different cross-sectional profiles that have higher surface area to lesser mass are often most useful to optimize mucoadhesion. These ratios, and the mucoadhesive effects, change as biodegradable materials degrade and their biomaterial characteristics change, which can also be exploited in balancing the residence time and clearance speeds.

In another variation, natural polymers may be used. Representative natural polymers that may be included in the devices include, but are not limited to, proteins, such as zein, modified zein, lectins, casein, gelatin, gluten, serum albumin, collagen and their derivatives, and polysaccharides, such as cellulose, chitin, chitosan, dextrans, polyhyaluronic acid and their derivatives. Hydrogel or sol-gel mixtures of polysaccharides may also be employed In some variations, the devices (or any portion thereof) may be made from a metal. Examples of suitable metals include, but are not limited to, cobalt, chromium, nickel, platinum, stainless steel, titanium, tantalum, and any of their alloys, e.g., nickel-titanium alloys, and combinations thereof. Furthermore, combinations of metal and polymeric devices, as in polymer coated nitinol structures, are also claimed.

II. Methods

Methods for treating sinusitis and its related respiratory conditions are also described. In general, the method involves placing a device as herein described within the OMC which delivers a therapeutically effective amount of the active agent locally to the OMC over a sustained period of time. The active agent may be delivered to any structure or tissue of the OMC depending on the device used, as described above. For example, the active agent may be delivered to the uncinate process, ethmoid bulla, middle turbinate, nasal wall, or any combination thereof. The active agent may be delivered over a period of about one week, about two weeks, about three weeks, about one month, about two months, or about three months or more. Different parts of the device may be configured to deliver the active agent over different time periods. Furthermore, different parts of the device may deliver different doses of the active agent. Similarly, a combination of shorter and longer term drugs or delivery doses may be used.

The device may be placed within the OMC by active fixation methods, passive fixation methods, or a combination of both methods. As previously mentioned, active fixation involves any method that places a device on or within a structure of the OMC and which visually alters the OMC anatomy. For example, methods that involve puncturing, piercing, and the like can be considered active fixation. As also previously mentioned, passive fixation involves any method that places a device within the OMC without visually altering OMC anatomy. For example, these methods may include space filling, space fitting, friction fitting, and tension fitting. A tool to aid visualization, e.g., an endoscope, may also be used during placement of the device.

III. Kits

The devices described here may be included in kits for delivering active agents to the OMC. In addition to any one of the devices described here, the kits may include a component that delivers the device or aids device delivery. For example, catheters (including guide catheters), guidewires, introducers, sheaths, and the like may be included in the kits. The catheters and guidewires may be malleable, pre-set in shape, or steerable. A lubricious coating, e.g., a Teflon™ or hydrogel coating, may also be provided on the outer or inner surface of the delivery device if desired, see, e.g., Thierry et al. Bioactive Coatings of Endovascular Stents Based on Polyelectrolyte Multilayers. *Biomacromolecules* 4:1564-1571 (2003). Other such devices may be delivered prior to their expansion or self-assembly by using techniques such as the Proetz procedure or vertical head position lavage or the OMC area, in which case kits may include a suitable liquid carrier for the device (e.g. saline rinse). Kits for certain colloidal devices, or with colloidal components, including many of those containing gels and foams formed soon prior to their use, may further contain a separate liquid or gas component within their respective kits. The kits may also comprise a temperature, humidity, and/or pressure controlled container.

The kits may include two or more types of devices. For example, space filling or self-assembling devices may be packaged with cannulating implants. With such a kit, the cannulating implant may be used to pierce and provide a port into a target area. For example, the space filling or self-assembling devices may then be delivered through the port into a sinus ostium or sinus cavity.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims. All patents, publications, journal articles, and other references cited herein are incorporated by reference in their entirety, as if each had been incorporated by reference individually.

What is claimed is:

1. A method for cannulating a portion of an osteomeatal complex comprising:
   implanting and securing a portion of a cannulating device to the osteomeatal complex by piercing a portion of the osteomeatal complex with a pointed tip of the cannulating device, wherein the cannulating device comprises a lumen extending at least partially therethrough and wherein the pointed tip of the cannulating device is implanted.

2. The method of claim 1 wherein the cannulating device is configured to release one or more active agents.

3. The method of claim 2 wherein the one or more active agents comprises an anti-inflammatory agent.

4. The method of claim 3 wherein the anti-inflammatory agent comprises mometasone furoate.

5. The method of claim 3 wherein the anti-inflammatory agent comprises fluticasone propionate.

6. The method of claim 1 wherein the cannulating device comprises a polymer coating.

7. The method of claim 6 wherein the polymer coating comprises one or more active agents.

8. The method of claim 1 wherein the cannulating device comprises a biodegradable polymer.

9. The method of claim 8 wherein the biodegradable polymer comprises a lactide/glycolide polymer.

10. The method of claim 1 wherein piercing the portion of the osteomeatal complex comprises piercing an ethmoid bulla.

11. The method of claim 1 wherein piercing the portion of the osteomeatal complex comprises piercing an anterior ethmoid cell.

12. The method of claim 1 wherein the cannulating device comprises a plurality of openings in a side of the cannulating device, wherein the openings are connected to the lumen.

13. The method of claim 1 wherein piercing a portion of the osteomeatal complex comprises piercing an ethmoid bulla and a septum between the ethmoid bulla and an anterior ethmoid cell to create a channel between the ethmoid bulla and the anterior ethmoid cell.

* * * * *